United States Patent [19]
Lopez-Berestein et al.

[11] Patent Number: 5,213,970
[45] Date of Patent: May 25, 1993

[54] METHOD FOR OBTAINING SOLUBLE ANTITUMOR FACTOR

[75] Inventors: Gabriel Lopez-Berestein, Houston; Jim Klostergaard, Kingwood; Jim Turpin, Houston, all of Tex.

[73] Assignee: Board of Regents, The University of Texas System, Austin, Tex.

[21] Appl. No.: 6,814

[22] Filed: Jan. 23, 1987

[51] Int. Cl.$^5$ .................... C12P 21/00; C12N 5/08; C07K 15/06; C07K 3/16
[52] U.S. Cl. .................... 435/70.4; 435/240.2; 435/240.23; 530/351; 530/412
[58] Field of Search .................. 435/68, 240.1, 240.2, 435/240.23, 70.4; 514/2, 21; 530/351, 412, 413

[56] References Cited

U.S. PATENT DOCUMENTS

| | | | |
|---|---|---|---|
| 4,495,282 | 1/1985 | Ohnishi et al. | 435/68 |
| 4,591,557 | 5/1986 | Keyes et al. | 435/68 |
| 4,650,674 | 3/1987 | Aggarwal et al. | 514/12 |

OTHER PUBLICATIONS

Kilbourn, "Inhibition of the Mitochondrial Respiration of Tumor Cells by Soluble Factors released by Activated Macrophages", Order #DA8419088, Diss. Abstr. Int. B, 1984, 45(5), 1424–5.

Klostergaard et al., "Effector Mechanisms of Human Monocyte-mediated Tumor Cytotoxicity in Vitro: Biochemical, Functional, and Serological Characterization of Cytotoxins Produced by Peripheral Blood Monocytes Isolated by Counterflow Elutriation", Cancer Res. V46, 2871-2875, Jun. 1986.

Matthews, "Production of an anti-tumor cytotoxin by human monocytes", Dialog/Cancer Lit 1986, Abstract 0304724, Hern/82015985.

Hammerstrom et al, "Soluble Cytostatic Factor(s) Released from Lymphokine-Activated Human Monocytes" Dialog/Cancer Lit 1986 Abstract 0304683 Hern/82015944.

Liang et al, "Human and Mouse Tumor Necrosis Factor Differ in their Reactivity with Neutralizing Antibodies" Dialog/Cancerlit Abstract 1597605 ICDB 86021531, 1986.

Kull et al, "Necrosin: purification and properties of a cytotoxin derived from a murine macrophage-like cell line", PNAS V81, 7932-7936, 1984.

(List continued on next page.)

*Primary Examiner*—David L. Lacey
*Assistant Examiner*—Geroge C. Elliot
*Attorney, Agent, or Firm*—Arnold, White & Durkee

[57] ABSTRACT

Disclosed herein is a novel antitumor factor, termed Human Monocyte Toxin, obtained by the precise activation of cells of monocyte/macrophage lineage. Monocytes are isolated in the absence of endotoxin by counterflow elutriation. HMT release can be triggered by exposure to low levels of 6-0-stearoyl muramyl dipeptide, lipopolysaccharide, phorbol myristate acetate or other known macrophage activating agents. Triggering results in the rapid release of HMT which requires transcription, translation, and intact secretory apparatus. The requirement for precise control of the triggering agent concentration is disclosed. HMT in serum-free supernatants can be resolved into two distinct species based on molecular sieving employing conventional or HPLC chromatography: minor species of 100–120 Kd, termed alpha, and the predominant form, beta, of 60–70 Kd. Beta-HMT has been further characterized as purified by chromatofocusing and HP ion-exchange LC, which indicate a moderately acidic nature. Beta-HMT demonstrates cytotoxic (cytolytic and/or cytostatic) activity against human and murine cell lines in vitro. Beta-HMT mediated lysis of targets does not involve detectable production $H_2O_2$ or $O_2-$, nor can it be blocked by pretreatment of the toxin with TLCK; however, reversible protease inhibitors partially block lysis when coincubated with the target cell and Beta-HMT.

10 Claims, 10 Drawing Sheets

OTHER PUBLICATIONS

Utushizaki et al, "Definition of tumor-necrosis factor and its production mechanism", Dialog File 154, Medline, 1986.

Liang et al, "Production and Characterization of Monoclonal Antibodies against Recombinant Human Tumor Necrosis Factor cachectin", Biochem. Bio Phys. Res. Commun V137, 847–854, 1986.

Chen et al, "Lipopolysaccharide (LPS) Stimulates Fresh Human Monocytes to lyse Actinomycon D–Treated WEHI-164 Target Cells via increased secretion of a monokine similar to Tumor Necrosis Factor", J. Immunology, V.135(6), 3978–3987, 1985.

Sone et al, "Potentiation of direct antitumor cytoxicity and production of tumor cytolytic factors in human blood monocytes by human recombinant interferon-gamma and muramyl dipeptide derivatives", Abstract, Medline/Dialog 1986.

Gifford et al, "Effects of Rabbit Tumor Necrosis Factor (TNF) On Cells", in *Biochemical Characterization of Lymphokines* Academic Press, 1980 pp. 307–312.

Aggarwal et al, (A), "Human Tumor Necrosis Factor", in *Methods in Enzymology*, v. 116, 448–456, 1985.

Klostergaard et al, "Human Monocyte Cytotoxins", Natural Immunity and Biological Response, V4(5), 1985 #256.

Klostergaard et al, (1986), Cancer Res., 46:662–669.

Carroll et al. (1982), Jrnl. Biol. Resp. Mod., 1:245–252.

Unsgaard (1979), Acta path. microbiol. scand., Sect. C, 07:141–149.

Matthews (1981), Immunol, 44:135–142.

Sone et al., (1984), Gann, 75:970–978.

Turpin et al. (1985), Apr. 1985. FASEB Abstract.

Kleinerman et al. (1985), Cancer Res., 45:2058–2064.

Dialog Search Report.

METHOD FOR OBTAINING SOLUBLE ANTITUMOR FACTOR

The government may have certain rights in the present invention pursuant to NIH grant BRSG 5511.

BACKGROUND OF THE INVENTION

1. Field of the Invention

The present invention relates generally to novel antitumor compositions and their use in treating tumor cells. More particularly, the invention is directed to a soluble antitumor factor released by precisely activated cells of monocyte/macrophage lineage and further to methods for its purification and use.

2. Description of the Related Arts

Recently, great interest has been shown by medical scientists in the identification and isolation of a variety of biologically-derived factors which have shown promise in the treatment of various disease states. Moreover, a number of such biological factors have been identified that demonstrate cytotoxic anticellular activities which are selective for neoplastic cells, thus holding the promise that such factors may provide additional weapons in the anti-cancer armamentarium.

Macrophages have been a particularly important focus of attention as an appropriate arm of host response that might be manipulated for the immunotherapy of neoplastic disease. This attention is warranted because of the ubiquitous distribution of these cells in tissues, and because of their demonstrated ability in vitro to mediate a lytic mechanism preferentially manifested on tumor cells (See, e.g., Fidler (1978), *Isr. J. Med. Sci.*, 14:177). More recently, the activation of macrophages by targeted agents in vivo has led to the eradication of metastatic foci in animal model systems (See, e.g., Fidler et al. (1982), *Cancer Res.*, 42:496; Lopez-Berestein et al. (1984), *Clin. Exp. Metastasis*, 2:127).

Characterization of the tumoricidal mechanism has been conducted by a number of laboratories, and a striking scope of pathways has been attributed to the effector cell. Although there is widespread agreement that under most circumstances the lytic mechanism is facilitated by contact between the macrophage and the target cell, in many systems this has been shown not to be obligatory.

In the human system, reports from several laboratories have described macromolecular cytotoxins derived from human monocytes and macrophages. For example, Reed and Lucas ((1975), *J. Immunol.*, 115:795) have described a 45 kilodalton toxin that arose apparently spontaneously after adherence of peripheral blood mononuclear cells. Matthews, in a 1981 report, demonstrated that adherent peripheral blood monocytes could release a cytotoxin after 20 hours of incubation with varying levels of endotoxin triggering of the monocytes. ((1981), *Immunol.*, 44:135). This toxin exhibited a molecular weight of 34 kilodaltons by molecular sieving chromatography.

In contrast to the results of Reed and Lucas and Matthews, Hammerstrom found that peripheral blood monocytes from BCG-vaccinated donors required up to 3-5 days of total in vitro incubation and 24 hrs. incubation with crude human lymphokine preparations to release cytostatic factors. ((1982), *Scand. J. Immunol.*, 15:331). Previous studies by Hammerstrom had shown that this protocol produced competent effector cells for direct tumor cell cytotoxicity. In further studies, two cytostatic factors were characterized and partially purified by Nissen-Meyer and Hammerstrom ((1982) *Infect. Immunity*, 38:67), and found to exhibit molecular weights of about 40 and 55 kd.

In 1983, Cameron reported that cytotoxic activity could be obtained spontaneously from peripheral blood monocytes cultured in vitro for five days ((1983), *J. Reticuloendo. Soc.*, 34:45). This factor(s) was shown to enhance host survival in animal tumor systems. However, little molecular characterization was conducted. In 1984 Sone et al. ((1984), *Cancer Res.*, 44:640), found that human alveolar macrophages could be triggered with LPS (lipopolysaccharide) or MDP (muramyl dipeptide) to release a cytolytic factor. The ability of alveolar macrophages to release the factor was found to persist for up to 48 hours. However, as with the studies of Cameron, no biochemical characterization of the factor was reported.

A number of human cell lines have been exploited as models of monocytes/macrophages. Some of these have been found to release cytotoxic macromolecules following appropriate triggering. For example, Gifford et al. ((1984), *J. Natl. Cancer Inst.*, 73:69) demonstrated that KG-1, HL-60, ML-2, and ML-3 lines could be induced with PMA (phorbol myristate acetate) to release cytotoxins; the principal species from the ML-2 line was found to be 40 kilodaltons. Armstrong et al. ((1985), *J. Natl. Cancer Inst.*, 74:1) used the THP-1 cell line which, following exposure to relatively high levels of PMA, elaborated primarily a 120 kilodalton cytotoxic species believed to be a neutral protease. Pennica et al. ((1985), *Nature*, 312:724) reported the cloning of a TNF alpha cDNA which apparently coded for about a 17 kilodalton protein.

Therefore, in general, the prior art has demonstrated the existence of numerous biological response modifiers, certain of which have shown promise as potentially useful clinical agents. Moreover, numerous such factors of monocyte/macrophage origin have been described and characterized to varying extents and are presently being investigated to determine their efficacy in treating tumors. The present invention is directed to a novel antitumor factor isolated from cells of macrophage/monocyte lineage which has been characterized both in terms of its biological and biochemical attributes. It is believed by the present inventors that this novel factor will provide an additional tool for the medical oncologist in the treatment of various tumors.

SUMMARY OF THE INVENTION

Accordingly, in its most general and overall scope, the present invention is directed to the identification, purification and characterization of a novel soluble antitumor factor, referred to herein as Human Monocyte Toxin (HMT), which is released by cells of macrophage/monocyte lineage that have been precisely activated with relatively low levels of macrophage activating agents. In more particular aspects, the factor is shown to have an alpha form which exhibits a molecular weight of between about 100 and about 120 kilodaltons, or a beta form which exhibits a molecular weight of between about 60 and about 70 kilodaltons, when the factor is subjected to molecular weight sizing, for example, by molecular sieving chromatography. The beta form is shown to be immunologically cross reactive with human tumor necrosis factor and has an isoelectric point of approximately 5.8, as determined by chromatofocusing. Biochemical characterization of the factor reveals that the activity of the beta form is not significantly inhibited in the presence of 2000 units/ml. of catalase, 700 ug/ml. of arginine hydrochloride, or 5 mM TAME (alpha-N-tosyl-L-arginylmethylester) or TLCK (alpha-N-tosyl-L-lysylchloromethylketone).

Further aspects of the present invention reveals that the factor may be substantially purified by a process which includes the steps of 1) obtaining cells of macrophage/monocyte lineage without exposure to endotoxin; 2) incubating the cells in a substantially endotoxin-free medium with an amount of a macrophage activating agent that is effective to trigger the release of the factor by the cells into the medium, to provide a factor-containing medium; and 3) separating molecules contained with the factor-containing medium according to their molecular weights or relative isoelectric points to provide a fraction which includes the factor in a substantially purified form.

Although it is believed by the present inventors that this factor may also be obtained from cells of non-human macrophage/monocyte lineage, in a preferred aspect of the present invention, human monocytes are typically employed. Moreover, to obtain the factor in its most purified form, monocytes are first isolated to be substantially free of cells which are not of macrophage/monocyte lineage. In a preferred method, such cells are isolated by counterflow elutriation. However, more conventional methods of monocyte isolation, for example, percoll or ficoll/hypaque gradient fractionation, may be employed for their isolation.

Three main aspects are of crucial importance to the successful isolation of this factor: The first is the isolation of the mononuclear cells under conditions scrupulously controlled for endotoxin contamination; the second is the use of endotoxin-free medium having a precisely controlled amount of macrophage activating agent to incubate the cells and thereby selectively trigger the release of the factor by the cells into the medium; the third is obtaining a purified monocyte population which is preferably representative of all monocyte subpopulations.

The use of endotoxin-free medium is crucial in that it has been found that incubating the cells in the presence of most commercially obtained medium, which is typically endotoxin-contaminated, will preferentially trigger the release of tumor necrosis factor and inhibit the production or release of the present HMT factor. Accordingly, the amount of macrophage activating agent employed must be carefully controlled to ensure that the activated macrophage cells will release HMT as opposed to tumor necrosis factor. Thus, it appears that cells which are activated in a manner to release tumor necrosis factor do not release HMT, and vice versa.

Numerous macrophage activating agents have been found to work well in the practice of the present invention. In particular, it is has been found that lipopolysaccharide (LPS), in dose ranges from about 3 to 1000 ng/ml, stearoyl muramyl dipeptide (SMDP), in dose ranges from about 30 to 1000 ng/ml, and phorbol myristate acetate, in dose ranges from about 30 to 300 pg/ml, are particular preferred for activating the obtained monocytes.

The final step of separating molecules contained within the factor-containing medium according to their molecular weights or relative isoelectric points may generally be performed by methods typically employed in the art for achieving such ends. For example, separation based upon molecular weight may conveniently be achieved by subjecting the factor containing medium to molecular weight fractionation by column chromatography, for example, using gel exclusion or other molecular sieving columns. Alternatively, where desired, molecular weight fractionation may be achieved, for example, by density centrifugation or gel electrophoresis. However, due to the relative ease of performing column chromatography, and its applicability to large scale isolation, it is believed that those in the art will typically prefer to employ such column techniques. Alternatively, or additionally, one may desire to employ techniques which are known in the art for fractionating molecules based on their relative isoelectric points. It has been found that the HMT of the present invention may be isolated by techniques which are typically directed to isoelectric point-based fractionation schemes. In this regard, it has been found that chromatofocusing provides an adequate basis for achieving fractionation based on isoelectric points.

Based on the ability of the present HMT factor to be recognized by antisera specific for human tumor necrosis factor, such tumor necrosis factor antibody may be employed to substantially purify the factor. Numerous methods are known in the art for isolating an antigen through the use of the corresponding antibody. Due to the fact that the human tumor necrosis factor antibody exhibits a strong binding immunoaffinity for the factor, it is believed that all such immunoaffinity techniques may be employed for isolation and purification of the factor.

However, in a preferred aspect of the present invention, the anti-TNF antibody is affixed to a solid support to thereby provide a support-bound anti-tumor necrosis factor antibody which may be employed to isolate the factor. Therefore, factor isolation is achieved by contacting the support-bound antibody with the factor-containing medium under conditions which will promote the formation of an immunocomplex between the antibody and the factor, to thereby provide a support-bound antibody/factor immunocomplex. After the antibody/factor immunocomplex is washed to remove non-specifically bound material, the factor is eluted from the complex to thereby provide the purified factor.

Alternatively, one may desire to proceed using a support which in itself has affinity for the antibody, such as a protein-A-containing solid support, which may be used to bind the anti-TNF antibody either before or after immunocomplexing with the factor-containing medium.

The present invention is further directed to compositions which are formulated to include the HMT factor and their use in treating tumors. Moreover, pharmaceutical compositions are contemplated which further include the addition of a pharmaceutically acceptable salt, diluent or carrier, such as a sterilized salt solution, for use in application to the tumor cells to be treated. As used herein, the word treated is meant to include all forms of treatment of tumor cells for either killing such tumor cells or alternatively reducing their viability or metastatic properties.

DETAILED DESCRIPTION OF THE INVENTION

I. Overview

Figure 1:
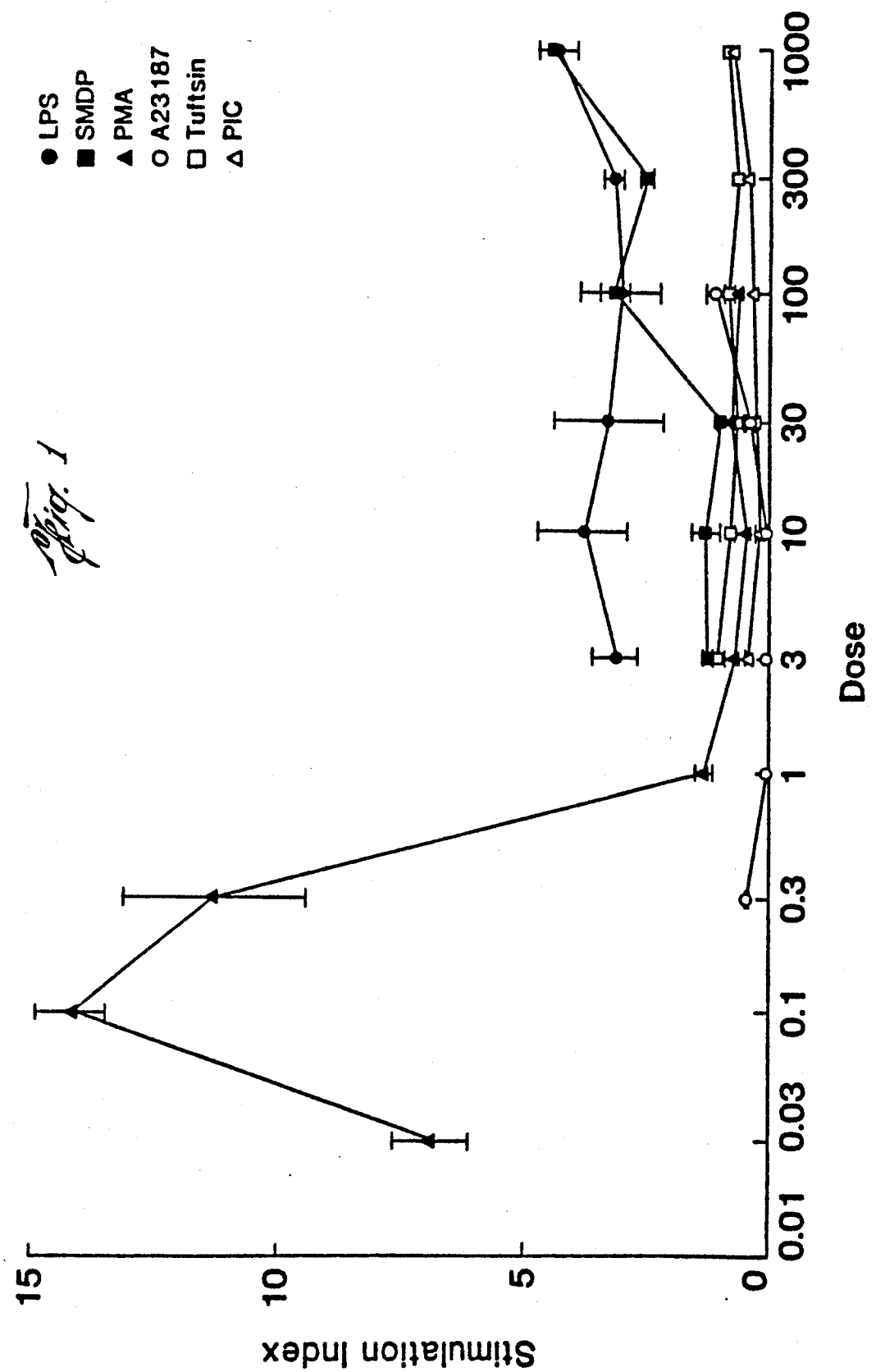
FIG. 1. Dose-response of various triggering agents on HMT production by peripheral blood monocytes. LPS (●) PMA (▲), SMDP (■), A23187 (○), tuftsin (□), and PIC (Δ) were incubated with freshly isolated monocytes, and the resulting lytic activity appearing in the supernatant 4 hrs. later was determined following dialysis. The lytic activity in each sample was normalized to the level released spontaneously, and the ratio, or stimulation index (mean±S.D.), is shown. The abscissa reflects values of nanograms/ml (ng/ml), except for the ionophore which is expressed in micromolar (um) quantities.

The present invention is directed to a soluble antitumor factor, termed Human Monocyte Toxin (HMT), which has been isolated to relative biological homogeneity by a process which is precisely controlled to selectively promote the production and release of HMT by cells of monocyte/macrophage lineage. Accordingly, one of the primary problems addressed by the present invention is the tendency of such cells to release an immunologically related factor, TNF, upon activation with relatively higher levels of various triggering agents, to the exclusion of the present factor. That is, when monocytes/macrophages are activated with relatively high levels of activating agents, such cells typically release relatively large amounts of TNF but fail to produce or release HMT. Accordingly, the invention is directed in part to disclosing conditions whereby HMT is selectively released by such activated cells.

In general terms, selective monocyte activation is achieved by ensuring that the cell-incubating and isolating medium is free of endotoxin, which in typically present in media in concentrations which will cause the release of TNF and inhibit the release of HMT, and by adding to such endotoxin-free medium a controlled amount of macrophage activator agent which amount is selected to insure preferential production and release of HMT.

The HMT of the present invention is shown to exert a cytotoxic effect on a wide variety tumor cells, including allogeneic and xenogeneic anchorage-dependent and independent tumor targets. Moreover, the HMT is isolatable from cells obtained from normal human donors, thus representing a ready source for preparing the HMT without resort to specified cell lines.

In general, the factor is obtained in a substantially purified form so as to be free of contaminating biological activities, by first obtaining cells of monocyte/macrophage lineage in a relatively pure state. That is, such cells are preferably isolated to be substantially free of other cell types to help ensure that contaminating activities will not be expressed into the cell culture medium upon activation of the isolated cells. It has been found that counterflow elutriation is one technique which provides monocytes in a substantially pure state representing the total monocyte population. However, other techniques such as density or bouyant gradient centrifugation, for example, percoll gradient centrifugation, may work sufficiently well to provide the factor in a biologically purified form.

The obtained cells are then incubated in a precisely controlled amount of a selected macrophage activator or activators to stimulate the cells to selectively express HMT, and not Tumor Necrosis Factor, into the culture supernatant. By precisely controlling the amount of macrophage activator employed, it has been found that HMT is the primary anticellular biological activity expressed by the activated monocytes into the supernatant.

This "conditioned" supernatant, which contains the factor in a biologically purified form, is then employed to provide the factor in a further purified form by subjecting the supernatant to molecular fractionation, for example, fractionation based on molecular weight or isoelectric points of the included molecules. Molecular characterizations of the factor disclosed herein will demonstrate to those of skill in the art various biochemical attributes which can be taken advantage of to purify the factor. For example, it is shown that the factor has a molecular weight of between 60 and 70 kilodaltons (beta form) or between 100 and 120 kilodaltons (alpha form), with the predominant beta form exhibiting an isoelectric point of about 5.8. Moreover, the factor is found to be immunologically cross reactive, although biochemically distinct from, Tumor Necrosis Factor, thus lending the ability to isolate or further purify the factor using immunological adsorption techniques.

II. Biological Characterization of HMT

A. Preparation of Factor-Containing Compositions

Target Cell Lines

The EMT-6 murine adenocarcinoma (Balb/c) was provided through the courtesy of Dr. A. Kallmann, Stanford University, Palo Alto, Calif. The A-375 human melanoma was provided through the courtesy of Dr. I. J. Fidler, The University of Texas M. D. Anderson Hospital and Tumor Institute at Houston, Tex. The K562 human erythroleukemia was provided through the courtesy of Dr. C. L. Reading, The University of Texas M. D. Anderson Hospital. The murine L-929, the HeLa human adenocarcinoma and the WI-33 human lung fibroblast were from American Type Culture Collection (Rockville, Md.). Normal mouse lung fibroblast cultures were established by mincing of aseptically removed lung of 8-day old mice. All cell lines were negative for microbial contamination and maintained on antibiotic-free DME-F12 with 10% fetal calf serum (FCS).

Reagents

Endotoxin screened RPMI-1640 tissue culture medium and pooled human AB serum were purchased from M. A. Bioproducts (Walkersville, Md.); endotoxin-screened FCS was obtained from Hyclone Co. (Logan, Utah); lactalbumin hydrolysate (LAH) and $Ca^{++}$, $Ma^{++}$-free phosphate buffered saline (PBS) were from Grand Island Biologicals Co. (Grand Island, N.Y.). Ficoll was purchased from Pharmacia Laboratories (Piscataway, N.J.) and Hypaque from Winthrop Laboratories (New York, N.Y.). Human albumin was purchased from Travenol Laboratories (Glendale, Calif.) as a 10% solution. All commercial media and solutions were purchased either as pyrogen-free or prescreened to contain less than 0.25 ng/ml of endotoxin with the Limulus Amebocyte lysate assay (M. A. Bioproducts). Phenol-extracted endotoxin (E. coli; serotype 0128:B12), PMA, (phorbol myristatic acetate) calcium ionophore A23187, tuftsin, actinomycin-D, and monensin were from Sigma (St. Louis, Mo.). PIC was from P. L. Biochemicals, Inc. (Milwaukee, Wis.). SMDP (stearoyl muramyl dipeptide) was provided through the courtesy of Dr. Gordon Jones, Syntex Laboratories, Palo Alto, Calif. Recombinant human IFN-gamma (rIFN-gamma) was obtained from Genetech (South San Francisco, Calif).

Microcytotoxicity Assays

The actinomycin D-treated L-929 target was employed in a microcytotoxicity assay as described by Fisch et al. (1983), *J. Immunol. Meth.*, 57:311; and Kilbourn et al. (1984), *J. Immunol.*, 133:1984; this was the standard rapid assay used throughout most of these studies, allowing evaluation of cytolytic effects after 18 hr of treatment. In brief, actinomycin-D treated L-929 target cells were established and after 1 hr. of drug treatment, the cultures were washed, and a range of monocytes was added (1-30×10³ monocytes/well). This procedure established a range of effector:target ratios of approximately 1:30-1:1. To one series of cultures, LPS (100 ng/ml) was added. After 18 hr. of incubation, cytotoxicity was evident microscopically, even with the lower effector:target ratios and was augmented with LPS-treated monocytes. L-929 targets that had not been actinomycin-D-treated, were also affected at 18 hr., but required higher effector cell numbers.

These observations, which indicated the high sensitivity of the actinomycin-D treated L-929 cell to the direct cytotoxic effects of activated human monocytes in a rapid assay, provided a significant rationale for the use of this target cell for the studies described below.

For the data reported for this target in Table 2, the assay was conducted identically except that actinomycin D was omitted, and cytotoxicity was allowed to proceed for 72 hr. Similarly, the EMT-6, HeLa, A-375, K562, WI-38, and lung fibroblast targets were seeded at 2.5-10×10³ cells/well in 100-200 ul of medium. After 24 hr., toxin (beta-HMT; see below) was added and incubation was continued for an additional 18-72 hr. Cytotoxicity in these cultures was evaluated after staining with neutral red or with 3-(4,5-dimethylthiazol-2-yl)-2,5-diphenyltetrazolium bromide (MTT).

Units/ml were calculated by linear regression as the reciprocal of the dilution that caused reduction of optimal density, for either stain, to 50% of control untreated cultures.

1. Monocyte Isolation

As noted above, it has been found that the most preferred method for monocyte isolation is by the technique known as elutriation. The elutriation procedure was performed in general as described by Contreras et al. ((1980), *Cell. Immunol.*, 54:215) and Sanderson et al. ((1977), *J. Immunol.*, 118:1409) as modified by Turpin et al. ((1986) *J. Clin. Apheresis*, 3: 111). The elutriation system was a Beckman (Palo Alto, Calif.) JE-6B centrifuge with elutriation rotor equipped with a standard separation chamber. Flow rate was controlled using a Cole-Parmer (Chicago, Ill.) unified drive variable-speed pump with a 10-turn micrometer dial. Sample loading and collection occurred in a laminar flow hood to maintain sterility.

Mononuclear cells were resuspended in cold (4° C.) elutriation media consisting of PBS without $Ca^{++}$ and $Mg^{++}$ supplemented with 0.1% human albumin, 0.22% sodium bicarbonate, and 20 ug/ml garamycin in a total volume of 500 ml. This media was determined to be LPS negative using standard detection systems. The cell suspension was counted and cell volumes were determined on a Coulter ZBI coupled to C-1000 channelizer with X-Y recorder (Coulter Electronics Hialeah, Fla.). The mononuclear cells (range from 1.5 to $6.0 \times 10^9$ with median at $2.5 \times 10^9$ cells) were loaded into the precooled (4° C.) and rpm stabilized (3,500 ±5) elutriation rotor at a flow rate of 33.0 ml/min. At this flow rate 98%±4% of the lymphocytes and all residual platelets and RBCs were eluted from the system. Separation was monitored at 100-ml collection volume intervals. Separation was considered complete when less than $1.0 \times 10^7$ mononuclear cells were present per 100 ml collection volume. This was determined using the Coulter ZBI and channelizer to determine cell number and size distribution of the eluted population.

The fraction containing total monocytes was centrifuged at 300 g for 10 minutes at 4° C. and resuspended in RPMI 1640 supplemented with 5% pooled human AB serum and 20 ug/ml garamycin (culture media). The elapsed time from the end of the plateletpheresis procedure to resuspending in culture media is 2-3.5 hours.

2. Differential Expression of TNF and HMT by Activated Monocytes

It has been found that in isolating the present HMT factor, care must be taken to ensure that a proper dose range of activator is employed—a dose which will promote the expression of HMT but not TNF. This is an important consideration in that experiments have shown that for every activator there exists a threshold concentration above which TNF expression occurs and HMT expression is suppressed. For example, in the case of LPS, a concentration of above 5 ug/ml will effectively shut down the expression of HMT while stimulating the expression of TNF. Moreover, other activators have been found to exhibit the same tendency. In general, it has been found that the presence of a $10^3$ to $10^6$ -fold higher concentration of activator than is maximal for HMT production will tend to cause the release of TNF to the exclusion of HMT production.

Figure 2:
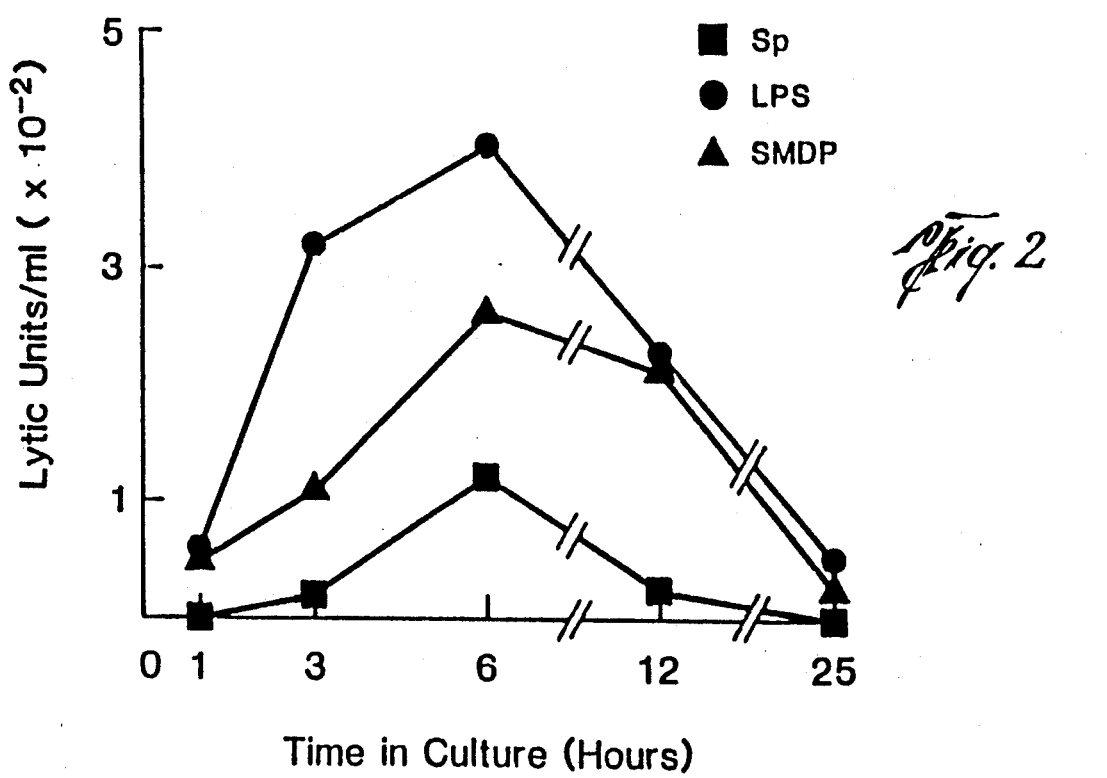
FIG. 2. Kinetics of HMT release from triggered monocytes. Monocytes were allowed to incubate with no triggering (spontaneous, SP) (■), or triggered with LPS (●) or SMDP (▲), and supernatants collected at various intervals thereafter, up to 25 hrs. Lytic activity in each sample is shown.

Of additional importance is the observation that the period of time the cells are incubated in the presence of an activator will have an effect on which factor will be expressed. For example, as shown in FIG. 2, maximal expression of HMT is found to occur within about 4 to 6 hours of incubation with the selected activator, yet by 24 hours, HMT production is found to virtually cease. However, TNF production, when an effective TNF-producing concentration of activator is employed, reaches its maximum at about 24 hours of incubation. Therefore, in addition to controlling the level of activator agent present, it may be desirable to collect the supernatant within 4 to 6 hours following activator addition, to further ensure the biological purity of the HMT subsequently expressed. Of course, by properly controlling the activator level, TNF expression is suppressed even upon longer incubation.

3. Demonstration of Antitumor Activity Released By Monocytes Following Macrophage Activation With Various Macrophage Activators For the standard preparation of HMT-containing supernatants, the following protocol was employed. Washed adherent peripheral blood monocytes, isolated as described above, were cultured for 4-6 hr. (FIG. 2) at 37° C. in endotoxin-screened medium (DME-F12) with 0.1% Lactalbumin hydrolysate (LAH) and 50-100 ng/ml of lipopolysaccharide (LPS) (FIG. 1). Monocytes were plated at a density of $4-6 \times 10^5/cm^2$ (FIG. 3) and release volume was 0.3-0.4 $ml/cm^2$. The supernatant was clarified by centrifugation and frozen at $-20°$ until further use. Supernatants obtained in this manner were not found to contain immunoprecipitable amounts of TNF.

However, to determine the proper HMT-inducing concentrations of other macrophage activators, a series of activation experiments were performed with varying amounts of recognized macrophage activators. Monocyte monolayers were established at $1 \times 10^6$ cells/2 $cm^2$ well in 24-well plates and treated with various triggering agents over a broad dose range: LPS, SMDP, tuftsin, and PIC (poly I-C) were employed at 3-1000 ng/ml, PMA at 0.03-1000 ng/ml, and the calcium ionophone A23187 at 0.3-100 uM. Control wells included medium alone. After 4 hrs., the supernatants were collected and the HMT present determined by bioassay. The results from several experiments were pooled; the ratio (mean±S.E.) of lytic activity in test supernatants compared to that spontaneously released (media alone overlaying monocytes) is expressed as a stimulation index in FIG. 1.

LPS, SMDP, and PMA all served as effective triggers for HMT release. LPS at levels as low as 3 ng/ml appeared to exceed a threshold for triggering; this threshold was achieved only with higher levels (100 ng/ml) of SMDP. PMA demonstrated a biphasic effect of HMT production; the optimum does was in the 100 pg/ml range, whereas higher levels (3-100 ng/ml) slightly suppressed spontaneous HMT release. In contrast, the ionophore A23187, tuftsin, and PIC were ineffective triggers in the dose ranges used in this particular experiment.

B. Biological Characterization

1. Kinetics of HMT Production

Monocytes established as above in 24-well plates were triggered with LPS or SMDP (100 ng/ml). Samples harvested at various times were frozen and then assayed for HMT activity at one time on L-929 cells to eliminate variability due to fluctuations in the sensitivity of the assay. Typical results from three experiments are shown in FIG. 2.

As can be seen from FIG. 2, HMT levels climbed rapidly after monocytes were exposed to the triggers, reaching a peak between 3-6 hrs. The levels declined thereafter, such that by 25 hrs. only 10% of the original activity remained. Only part of this decline can be attributed to slight instability to storage at 37° C.; this suggests HMT degradation occurs in the continued presence of the monocyte.

2. Effect of Monocyte Density on Production of HMT

Monocytes were seeded in 24-well plates at different densities, the highest being $4 \times 10^5/cm^2$. The wells were washed after the adherence step, and medium or medium with endotoxin was replaced; after 3 hrs., the supernatants were harvested and assayed for lytic activity on L-929 cells. The units (mean±S.E.) compared with density are shown in FIG. 3 for two experiments.

Figure 3:
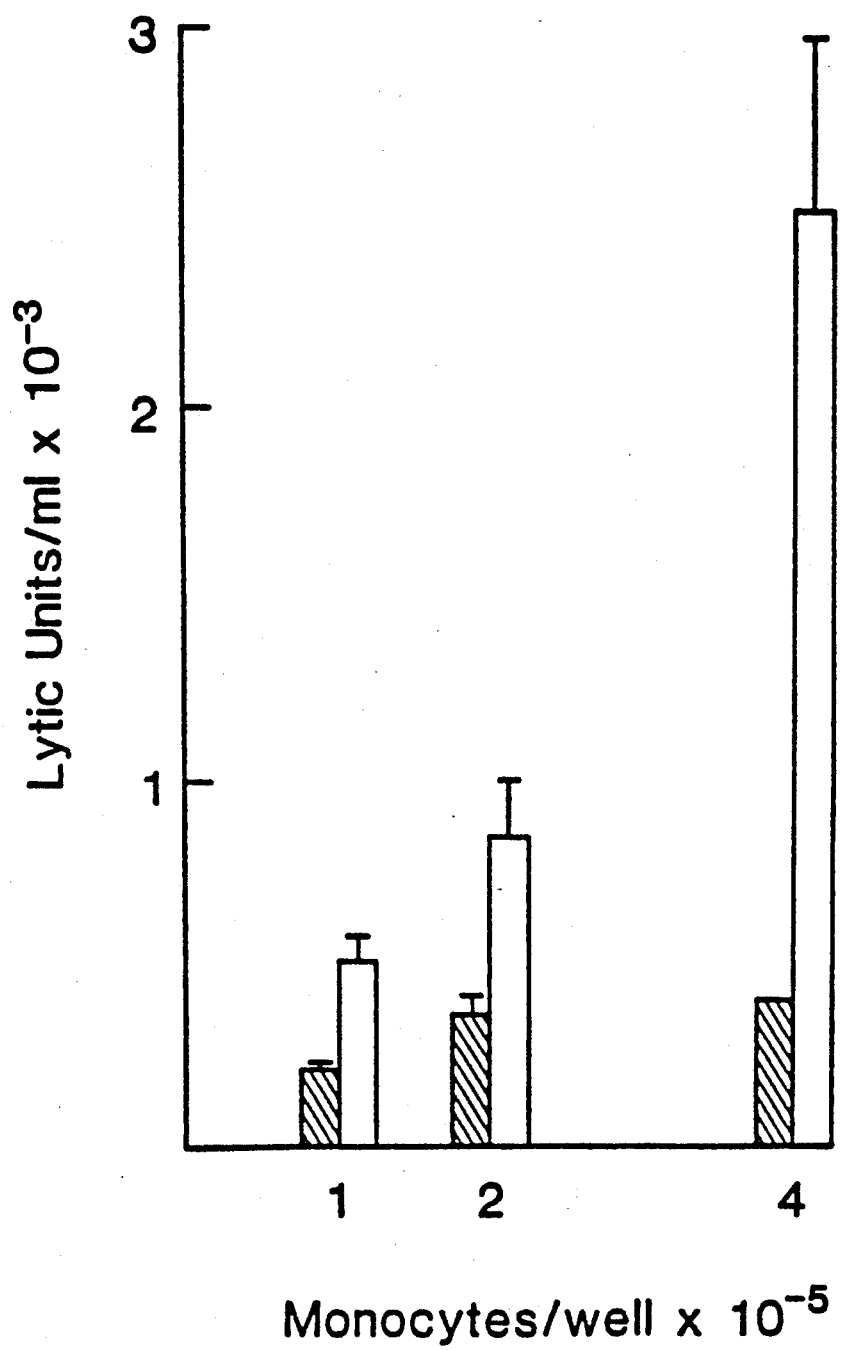
FIG. 3. Effect of monocyte density of HMT production. Monocytes were established on plastic as monolayers of different densities; HMT released spontaneously (hatched bars) or in response to LPS triggering (open bars) was determined by bioassay (mean±S.E.).

As can be seen from FIG. 3, HMT production could be detected spontaneously from as few as $1 \times 10^3$ cells/cm$^2$. Over the range tested, the activity recovered was virtually proportional to monocyte density. The optimal level of production was achieved with the highest level of monocytes seeded, $4 \times 10^5$ cells/cm$^2$. At this level, LPS-triggered monocytes released approximately 6-fold higher levels of HMT than occurred spontaneously. These results indicated that on the basis of surface area optimal conditions for HMT production required essentially confluent monocyte monolayers ($4-6 \times 10^5/cm^2$).

3. Role of Adherence on Monocyte Production of HMT

In a single experiment, monocytes at a density of $1 \times 10^6/ml$ were seeded in a 100 mm polystyrene dish or a 15 ml polypropylene tube. After 1 hr the polystyrene dish was washed free of growth medium, and the medium replaced with medium containing LAH. Similarly, the polypropylene tubes were subjected to centrifugation to pellet the monocytes, and the monocytes were resuspended in medium containing LAH. After triggering with LPS, HMT release was allowed to occur for 4 hrs, at which time the supernatants were collected from either production source, centrifuged to clarify free of cells, and subjected to bioassay. The bioassay revealed that there was no significant difference between the levels of HMT produced by monocytes adherent to polystyrene and monocytes cultured on polypropylene surfaces. Thus the poor adherence which monocytes express on a polypropylene surface does not effect their ability to product HMT in comparison to monocytes which are strongly adherent to polystyrene.

4. Requirement for Transcription, Translation and Secretion following LPS-triggering of Monocytes for HMT Production/Release Monocytes were seeded in 24-well plates ($1 \times 10^6$ cells/well) and were washed after adherence. Actinomycin D, cycloheximide, or monensin was added in medium over a dose range of 0.03 to 10 ug/ml. After a 30 min. incubation, LPS (100 ng/ml) was added to the cultures. The resulting HMT in supernatants harvested 4 hr. later and then dialyzed was quantitated by bioassay on L-929 cells. The units of lytic activity in test cultures compared to a control LPS-triggered, non-drug-treated culture, was expressed as a percentage and the results from several experiments were plotted in FIG. 4.

Figure 4:
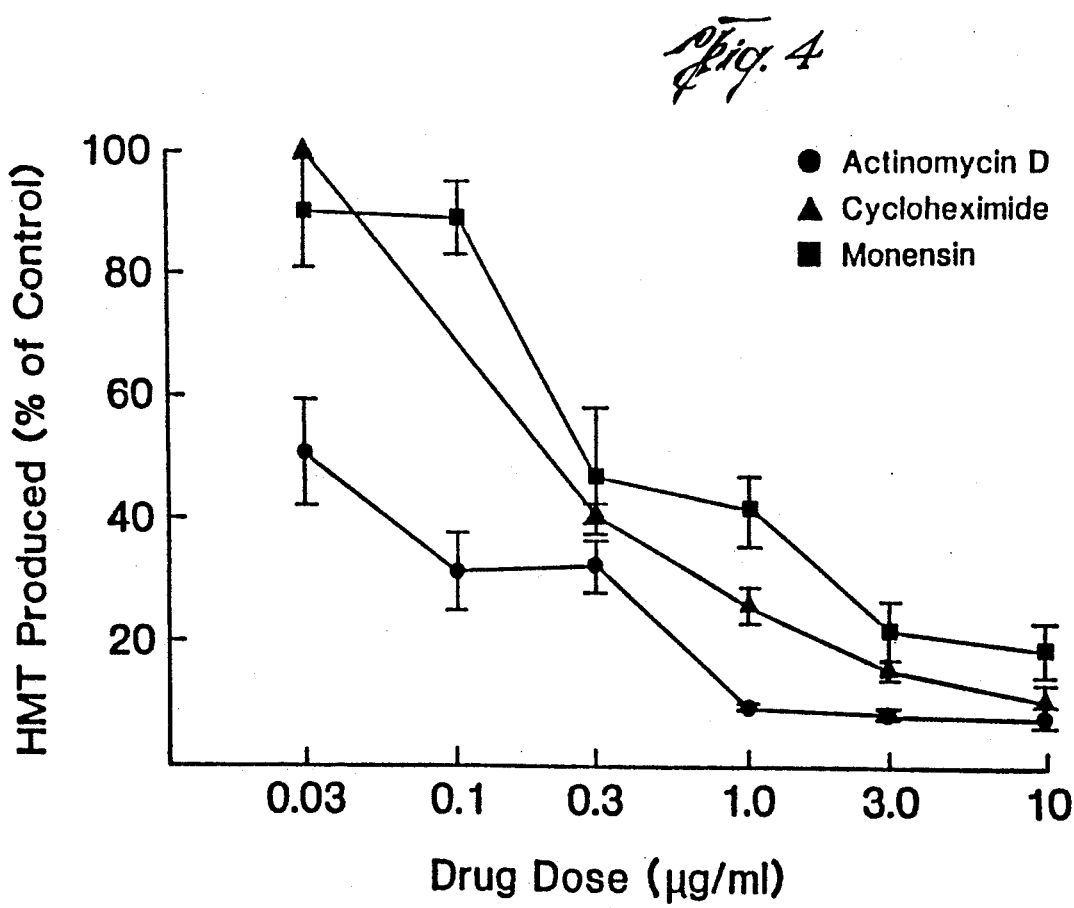
FIG. 4. Effect of drugs inhibiting RNA and protein synthesis and secretion on HMT release by LPS-triggered monocytes. Monocytes were pretreated with actinomycin D (●), cycloheximide (▲), and monensin (■) prior to LPS triggering The 4 hr. supernatants were dialyzed and assayed for lytic activity. The lytic activity recovered compared to an LPS-triggered, non-drug-treated control is expressed as a percentage (mean±S.E.).

As can be seen from FIG. 4, at the lowest level tested (30 ng/ml), actinomycin D caused 50% inhibition of HMT production. As expected from this result, cycloheximide was also found to inhibit HMT production (50% inhibition at 200 ng/ml). Secretory processes perturbed by monensin also appeared to be necessary for HMT appearance in monocyte supernatants, since this drug caused 50% inhibition at around 300 ng/ml. Interestingly, drug doses from 1.5 to 2.5 log 10 higher than the 50% inhibitory dose still allowed HMT production/release at 10-20% of control levels.

5. HMT Levels Produced by LPS-Triggered Monocytes from Randomly Selected Normal Donors.

Monocytes obtained from randomly selected normal donors undergoing routine platletapheresis over approximately 18 months were used to produce HMT by the standard protocol described above using LPS as the trigger. The supernatant samples were stored frozen at $-20°$ C. (under which conditions HMT is stable) until bioassay could be conducted on all accumulated samples at one time to eliminate assay to assay variability. The results are shown in Table 1 as units of lytic activity per ml (mean±S.E.). The supernatants demonstrated HMT levels that varied over two orders of magnitude. No alteration in technique reasonably accounted for this striking variability.

TABLE 1

Ability of endotoxin to induce HMT[a] from peripheral blood monocytes obtained from random normal donors

| Donor | Lytic Activity (Units/ml; Mean +/− SE)[b] |
|---|---|
| A | 137 ± 15 |
| B | 739 ± 166 |
| C | 123 ± 27 |
| D | 97 ± 5.3 |
| E | 362 ± 127 |
| F | 394 ± 138 |
| G | 6277 ± 22 |
| H | 291 ± 108 |
| I | 358 ± 3 |
| J | 769 ± 218 |
| K | 890 ± 274 |
| L | 436 ± 2 |

[a]Supernatant release after 4 hours of LPS (50-100 ng/ml) treatment immediately after adherence.
[b]Determined on L-929 targets.

6. Attempts to Mature Monocytes from Initially Pheresed Normal Donors for HMT Production by Further in vitro Culture with rIFN-gamma In two separate experiments, monolayers of monocytes from normal donors with no known history of pheresis were established in microwells. Some cultures were stimulated immediately with LPS (50 ng/ml) for 4 hr. after adherence; other cultures were incubated in serum-containing medium with or without rIFN-gamma (0.01-1.0 units/ml) for 1, 5, or 9 days. These sets of cultures were then washed, and triggering of HMT release by LPS was attempted. The supernatants obtained from all cultures were frozen at $-20°$ until bioassay on one set of L-929 targets. The units/ml of lytic activity (mean±S.E.) for each sample is shown in FIG. 5.

Figure 5:
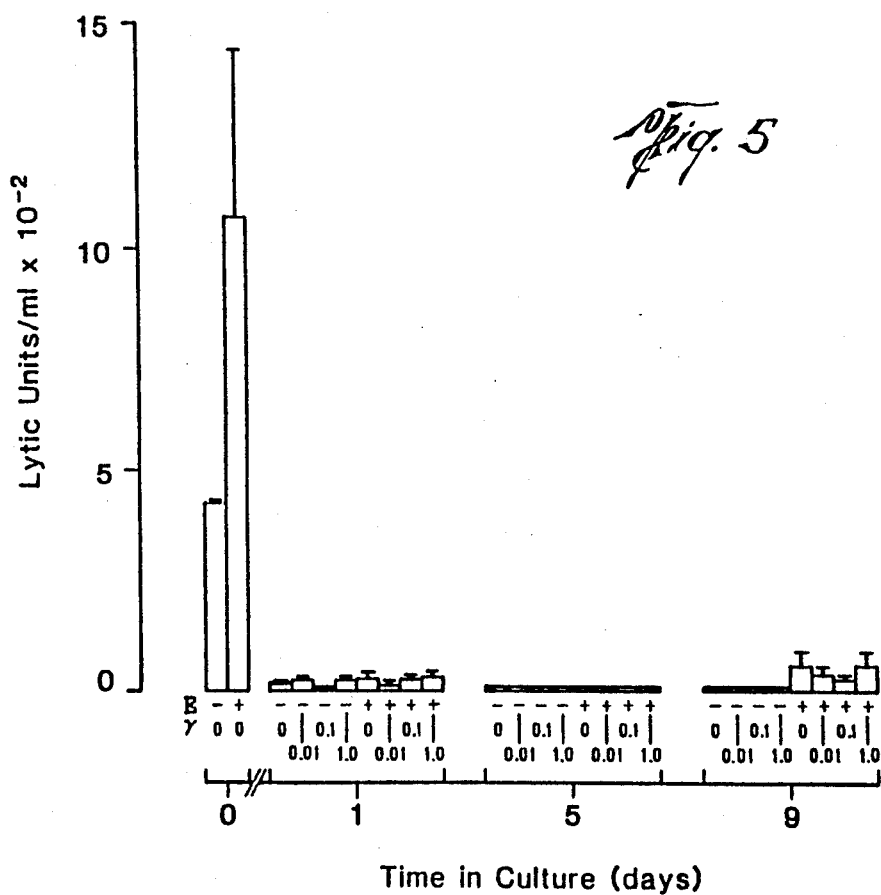
FIG. 5. Attempts to mature monocytes from initially pheresed normal donors by in vitro culture. Monocytes were cultured in medium alone (E−) or were triggered with endotoxin (E+) either immediately following a 30 min. adherence period, or after culture for up to nine days in the presence of media alone or up to 1.0 unit/ml of rIFN-gamma. Resulting lytic activity in the supernatant following a 4 hr. release period (mean±S.E.) is shown.

As shown is FIG. 5, monocytes, when initially isolated, released HMT spontaneously and even higher levels could be achieved in response to LPS-triggering. However, monocytes that had been further cultured in vitro for 1, 5, or 9 days alone or with any level of rIFN-gamma tested no longer released significant levels of HMT either spontaneously or after exposure to LPS. Monocytes cultured under these conditions appeared to be intact morphologically and demonstrated high viability (greater than 95%).

7. Attempts to Mature Monocytes from Recently Pheresed Normal Donors for HMT Production by Further in vitro Culture with rIFN-gamma In two separate experiments, monolayers of monocytes isolated from plateletapheresis residues from normal donors who had undergone plateletapheresis up to one week earlier were established in microwells. Some cultures were stimulated immediately with LPS (50 ng/ml) for 4 hr. after adherence; other cultures were incubated for up to 168 hr. in serum-containing medium with or without rIFN-gamma (0.1 or 1.0 units/ml). IFN treatment was confined to the last 24 hr. interval immediately preceding washing and LPS triggering in the results shown in FIG. 6. The supernatants were harvested and frozen at −20° until bioassay as above. The units per ml of lytic activity for each sample is shown as well in FIG. 6.

Figure 6:
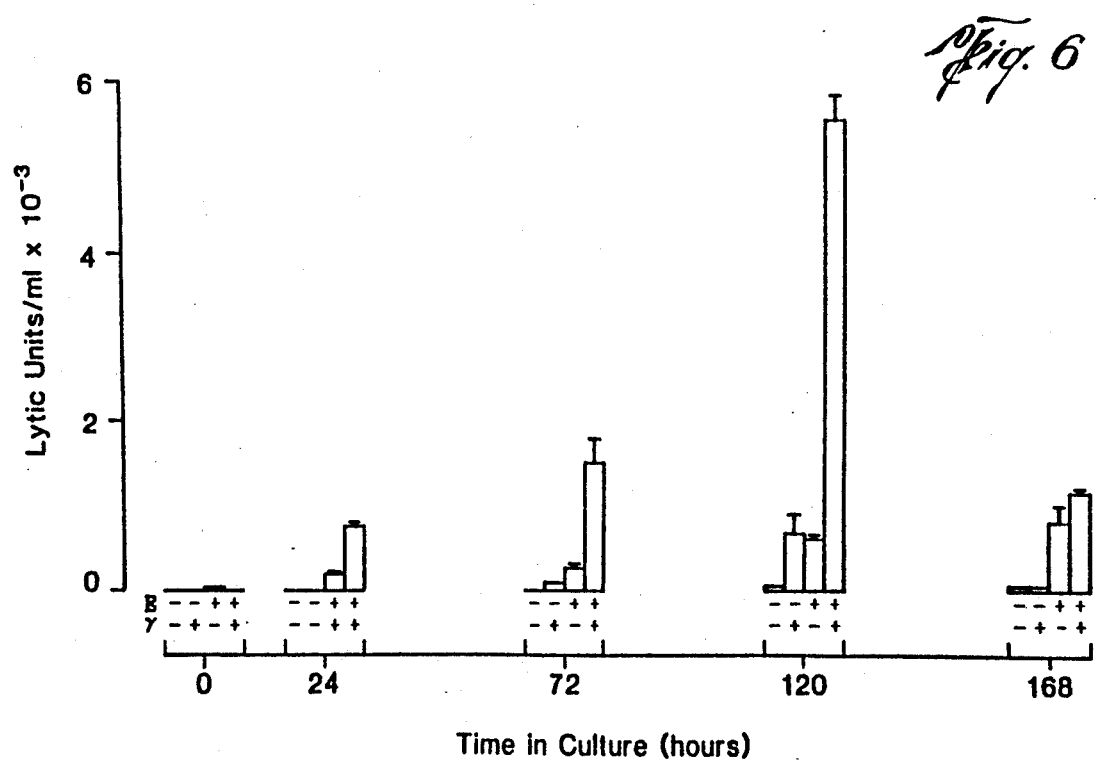
FIG. 6. Attempts to mature monocytes from recently pheresed normal donors by in vitro culture. Monocytes were cultured essentially as in the experiment shown in FIG. 5, except that total culture time was a maximum of 168 hrs., and rIFN-gamma treatment (1.0 unit/ml) was confined to the last 24 hrs. HMT lytic activity in supernatants following a 4 hr. release period is shown (mean±S.E.).

As will be appreciated from FIG. 6, in contrast to the monocytes obtained from donors who were initially pheresed, monocytes from donors with a recent pheresis history were initially incapable of HMT release, even when triggering was attempted with LPS. However, rIFN-gamma (1.0 unit/ml) showed a marked ability to prime the monocytes for LPS triggering when cultured for up to 5 days; this ability was transient and declined thereafter. The levels of HMT achieved with monocytes from this type of donor and with rIFN-gamma maturation were consistently higher (2500–5500 units/ml) than those observed when using monocytes from initially pheresed donors (400–1200 units/ml) (FIG. 5 and Table I).

Figure 7:
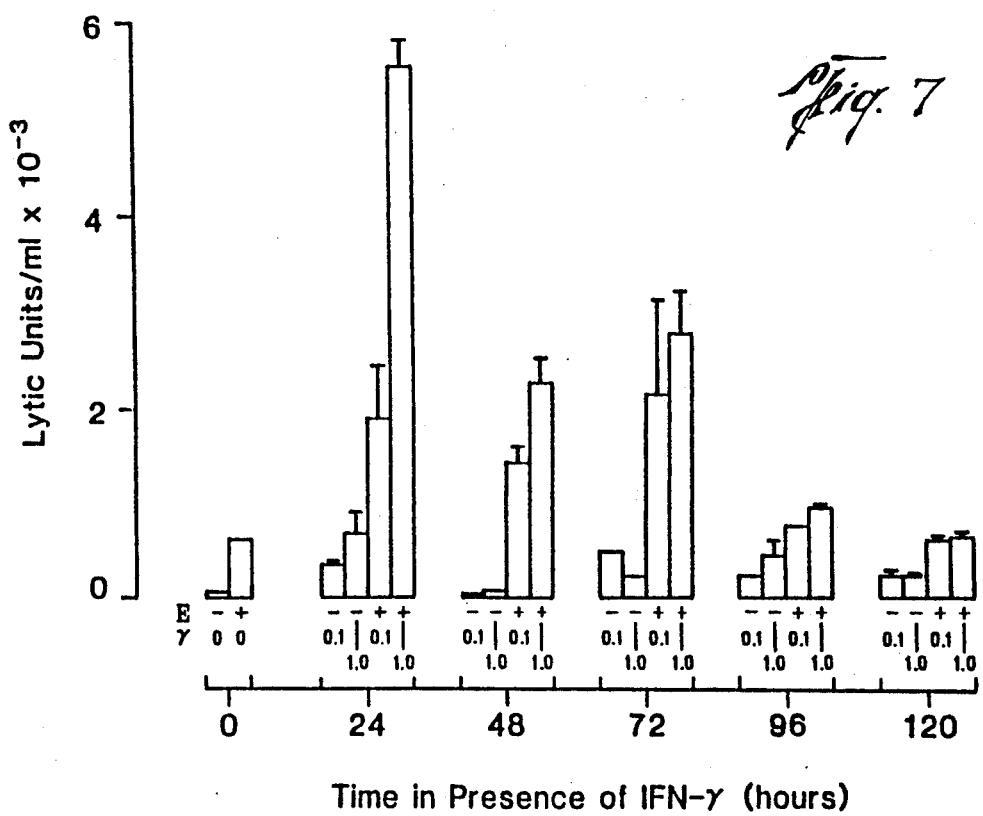
FIG. 7. Effect of varied duration of rIFN-gamma treatment on monocyte priming for HMT release. Monocytes isolated form the donors of FIG. 6 were cultured in medium for 120 hrs.; during this incubation period, rIFN-gamma (0.1 and 1.0 units/ml) was added either initially (120 hr. total treatment) or at 24 hr. intervals up to 24 hrs. before endotoxin (E) triggering. Some cultures were not treated with rIFN-gamma (0 hrs.). HMT lytic activity (units/ml) in each culture was determined (mean±S.E.).

Monocytes cultured for up to 168 hrs. in vitro were incubated for various times with rIFN-gamma up to the time of washing and LPS (50 ng/ml) triggering. Supernatants were collected after 4 hr. of triggering and then frozen at −20° until assayed on one set of L-929 cells. The units per ml for monocyte cultures incubated in vitro for a total of 120 hr. is shown in FIG. 7.

The optimal time of rIFN-gamma treatment was the 24 hr. interval just before LPS triggering; with somewhat longer exposure, the monocytes become less responsive to LPS, and by 120 hrs. the effect of rIFN-gamma was completely reduced to a pretreatment state of responsiveness.

8. Initial Characterization of Anticellular Effect of Beta-HMT

The principal species of HMT, the beta-class, was isolated as described in Section III below. A single preparation of beta-HMT was used in several cytotoxicity assays with a number of target cells (see Table 2); L-929, L-929 with actinomycin D treatment, EMT-6, A375, K562, HeLa, WI-38 and normal lung fibroblasts. These targets showed a spectrum of sensitivities to beta-HMT; the lung fibroblasts, WI-33 and EMT-6 were refractory, while the human tumor targets were intermediate in sensitivity. The effect on K562 appeared morphologically and by neutral red staining to be primarily cytostatic. The L-929 target in a 72 hr. assay appeared to be of highest sensitivity; when treated with actinomycin D for measurement of cytolysis in the standard 18 hr. assay, its sensitivity increased by about one order of magnitude. The data obtained from these experiments is compiled in Table II.

TABLE II

| Cytotoxic effects of HMT[a] on Allogeneic and xenogeneic target cells in vitro | |
|---|---|
| Target | Lytic Units/ml |
| L-929[b] | 93 ± 21 |
| L-929 (Actinomycin D)[c] | 349 ± 128 |
| EMT-6[c] | <<15 |
| K562[b] | 22 ± 4 |
| A375[b] | 26 ± 5 |
| HeLa[b] | 16 ± 3 |
| WI-38[c] | <<10 |

TABLE II-continued

| Cytotoxic effects of HMT[a] on Allogeneic and xenogeneic target cells in vitro | |
|---|---|
| Target | Lytic Units/ml |
| Mouse Lung Fibroblasts[d] | 15 |

Figure 8:
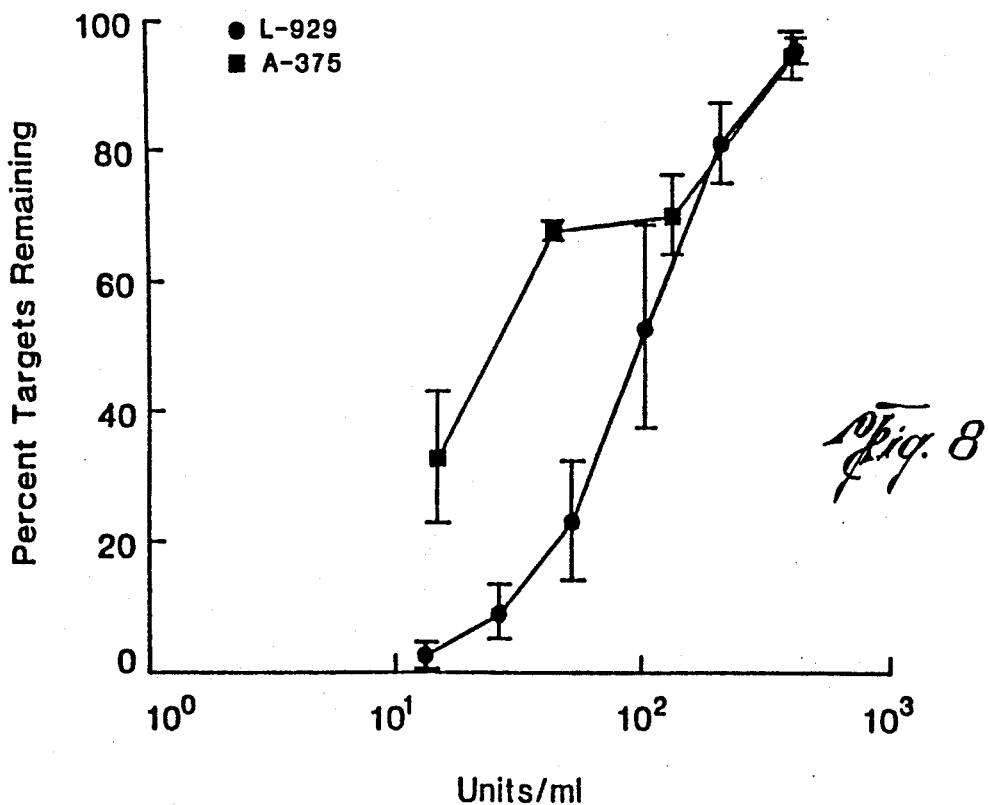
FIG. 8. Dose-response of beta-HMT lytic activity on tumor target cells. A single preparation of beta-HMT was assayed by serial dilution on cultures of murine L-929 fibroblast-like targets (●) and on A-375 human melanoma targets (■) . The extent of cytotoxicity in 72–96 hrs. was determined using the MTT assay, and expressed as the percentage of untreated control cultures. The abscissa represents the activity in units/ml that the beta-HMT preparation exerted on the targets.

[a]The 60–70 kd beta-HMT class was isolated by gel filtration of concentrated supernatants of LPS-triggered human monocytes as described. A single pool of HMT was used in these experiments to minimize variability.
[b]72 hr. assay, MTT stain
[c]18 hr. assay, neutral red stain
[d]48 hr. assay, neutral red stain The differential sensitivity of the A375 and L-929 targets is further evidenced in FIG. 8. A single preparation of beta-HMT was titered on these targets and the percentage of targets remaining after 72–96 hrs. at each dilution was determined by the MTT assay. In the single experiment shown, to achieve 50% reduction compared with controls required four times as much beta-HMT on A375 compared to L-929 targets, as this preparation scored at 26 units/ml on the A375, and 93 units/ml on the L-929 targets.

The foregoing studies demonstrated that under these conditions of isolation of highly purified, functionally intact monocytes, with strict control for endotoxin contamination, these effector cells can be rapidly promoted to demonstrate tumoricidal capacity, with release of a lytic macromolecule(s). This characteristic may reflect the responsiveness to triggers for activation of monocytes in vivo. The observation that monocytes from donors having undergone recent pheresis show poor initial LPS responsiveness, which may, however, be markedly enhanced after in vitro cultivation with rIFN-gamma, is remarkable. Prior manipulation presumably causes demargination or more rapid emigration from the bone marrow of cells of the monocyte lineage. A direct interpretation is that the immature monocytes lack priming in vivo to become LPS triggered for tumoricidal capacity, which can be overcome by rIFN-gamma in vitro. Indeed, the presence of subpopulations of immature monocytes defined by centrifugal elutriation has been demonstrated for oxidative burst expression (Turpin et al. (1986), J. Immunol., 136: 4194).

However, why a similar maturation was not observed with monocytes from donors who initially underwent pheresis is unclear, as these monocytes should have a significant immature subpopulation that may become primed in vitro. This finding raises the possibility that the mature populations are regulating the response of the immature monocytes to priming signals. Furthermore, aside from the pheresis history of the donor, there are certainly additional factors that influence the initial LPS-responsiveness of the monocytes populations; their existence is suggested by a low correlation coefficient (<0.2) that has been observed between the lytic activity released by these LPS-triggered monocytes and either the time since last pheresis or the total number of prior pheresis donations; this relationship was established for donors evaluated over 18 months.

In Section III below, biochemical and functional characterizations of HMT are disclosed. Two activities in the monocyte supernatants appear to constitute the lytic species: the larger form (100–120 kd) termed alpha is present in lower amounts than the predominant beta form (60–70 kd). However, biochemical studies indicate that beta-HMT does not appear to be a neutral protease or arginase.

III. Biochemical Characterization

A. Purification of HMT

1. Purification of Human Peripheral Blood Monocytes (HPBM)

Monocytes were isolated from normal donors undergoing routine plateletapheresis by counterflow elutriation as described in Section II above.

These highly purified HPBM were plated at a density of 500,000/cm$^2$ on plastic dishes (100×20 mm, Costar, Cambridge, Mass.) and allowed to adhere for 30 min. at 37° in the presence of fetal calf serum. Thereafter, the washed monolayers were triggered with lipopolysaccharide, and HMTs were recovered in the supernatant in the subsequent 4-6 hr of culture in serum-free medium.

2. Partial Purification of Monocyte Supernatants

The cell-free supernatants were concentrated on a YM10 membrane (Amicon Corp., Danvers, Mass.). These concentrates were then subjected to molecular sieving on Sephacryl S-200 and the resulting fractions tested for bioactivity. The column measured 2.5×45 cm and Dulbecco's phosphate buffered saline buffer (DPBS) was employed at a flow rate of 30-40 ml/hr. Two milliliter fractions were collected. Molecular weight markers included blue dextran (2×10$^6$ kD), immunoglobulin (150 kD), hemoglobin (64 kD), and cytochrome C (12 kD). The fractions were assayed for lytic activity on actinomycin D-treated L-929 target cells, as described in Section II above.

Figure 9:
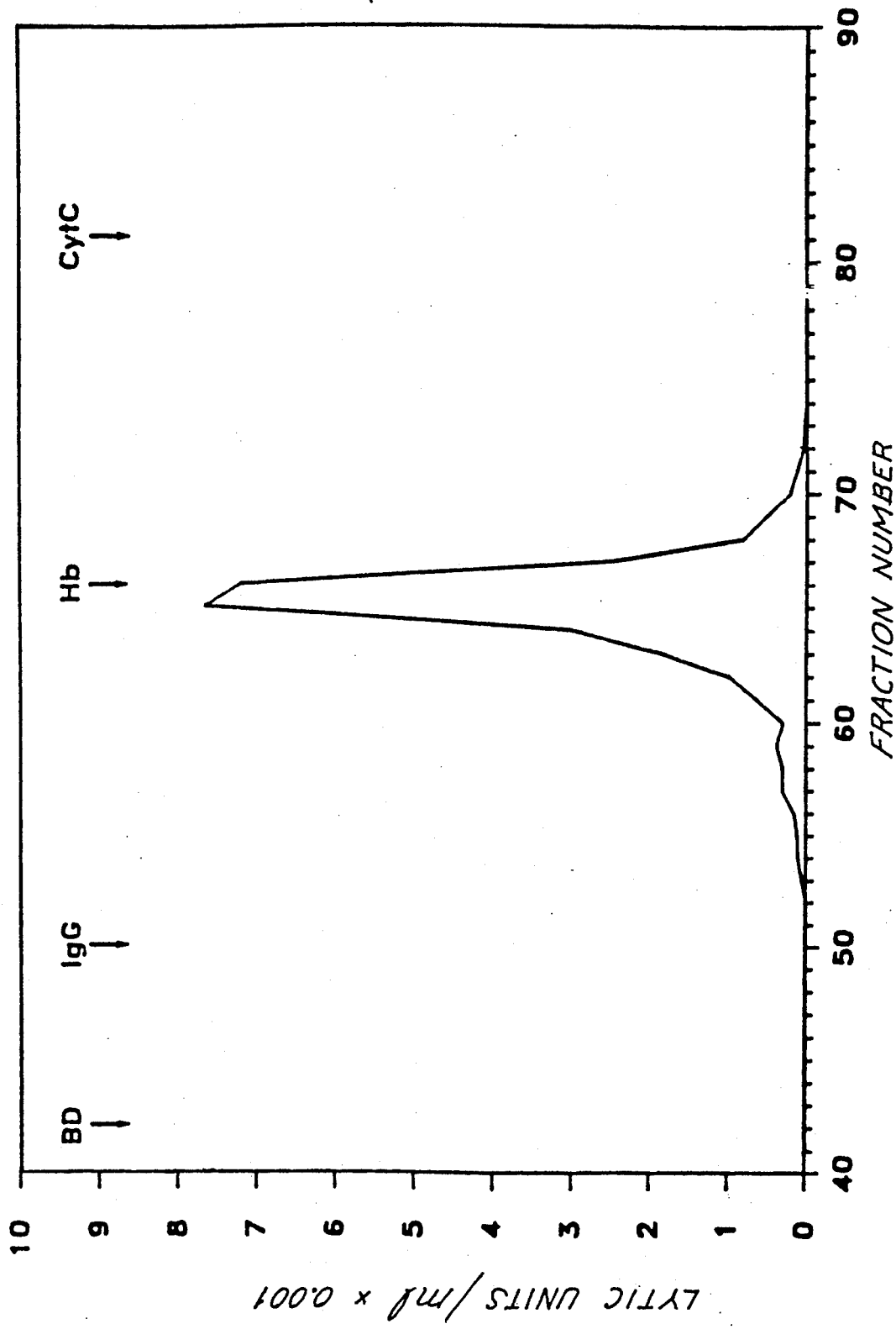
FIG. 9. Supernatants from LPS-triggered human monocytes were concentrated on a YM-10 membrane and subjected to molecular sieving on Sephacryl S-200. Fractions were tested for biological activity on L-929 cells. Molecular weight markers (Blue Dextran; BD, $2\times10^6$ kD; immunoglobulin G, IgG, 150 kD; hemoglobin, Hb, 64 kD; cytochrome C, CytC, 12 kD) are shown.

In FIG. 9 are plotted the lytic units per ml of each fraction obtained by sieving. The major peak of lytic activity is clearly in the 60,000-70,000 Dalton range, based on its migration compared to the molecular weight markers blue dextran, IgG, hemoglobin, and cytochrome C. A very minor peak, which in this run appeared as a leading shoulder of the major peak, is almost invariably observed as well. The higher molecular weight peak has been designated alpha-HMT, and the lower molecular weight peak beta-HMT.

Figure 10:
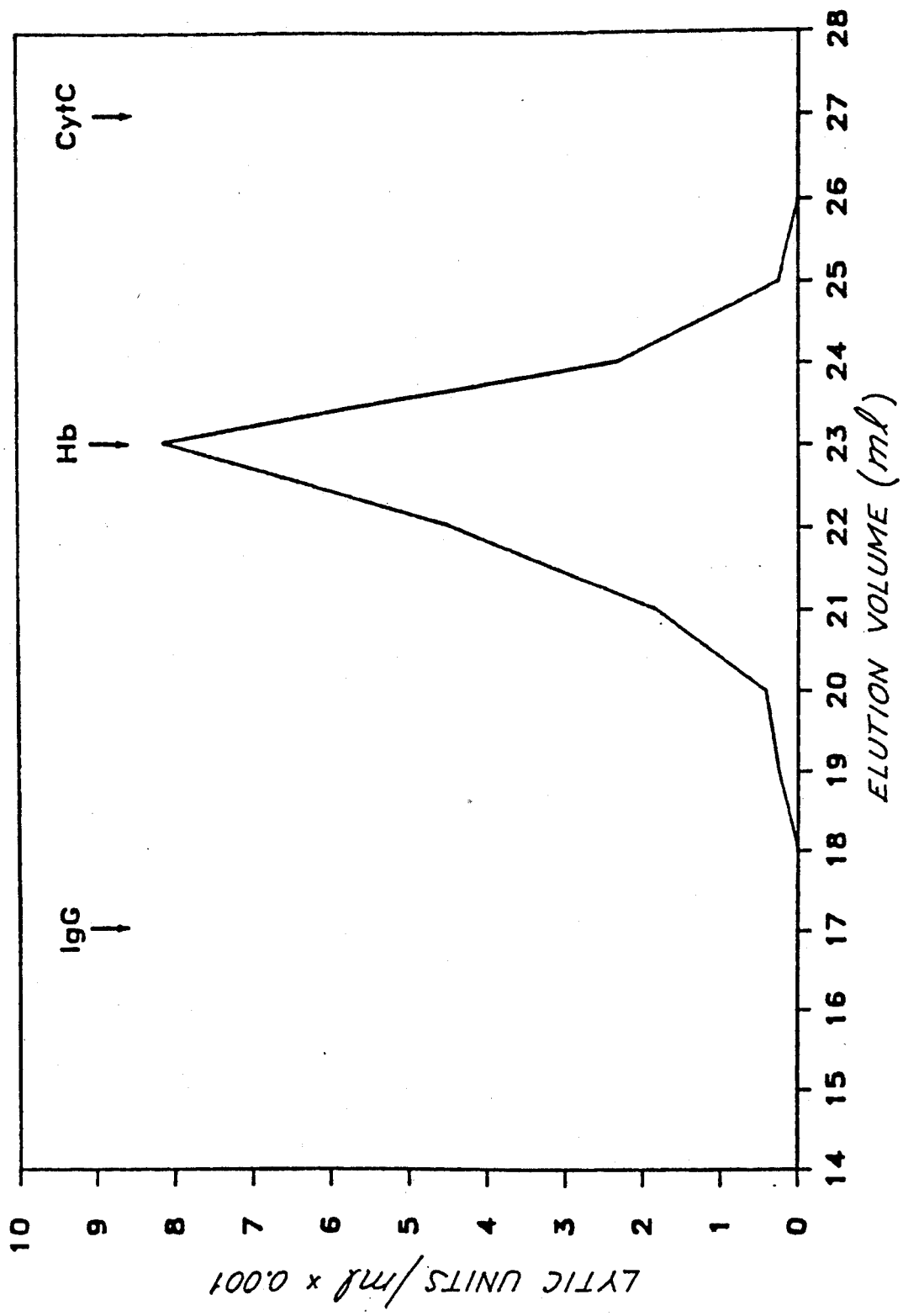
FIG. 10. Supernatants from LPS-triggered human monocytes were filtered prior to injection into a TSK-3000 column. Each fraction was tested for biological activity on L-929 cells. Molecular weight markers are shown.

Similar results were observed when an HPLC 3000 SW column (LKB) was employed as a matrix. Samples of cell-free HPBM supernatants (0.25 ml) were injected into an Ultro Pac TSK-G 3000 SW column (7.5×600 mm; LKB, Bromma, Sweden) equipped with a 7.5×75 mm precolumn. A 50% DPBS buffer system was employed with a flow rate of 0.5 ml/min.; one ml fractions were collected. Molecular weight markers were immunoglobulin G, hemoglobin, and cytochrome C. As seen in FIG. 10, a single predominant peak migrating in coincidence with hemoglobin is observed under these conditions. The beta-HMT species is the principal one obtained from LPS-triggering of monocytes either from initially pheresed donors or from monocytes from recently pheresed donors matured in vitro and pulsed with IFN-gamma.

3. Chromatofocusing of beta-HMT

Figure 11:
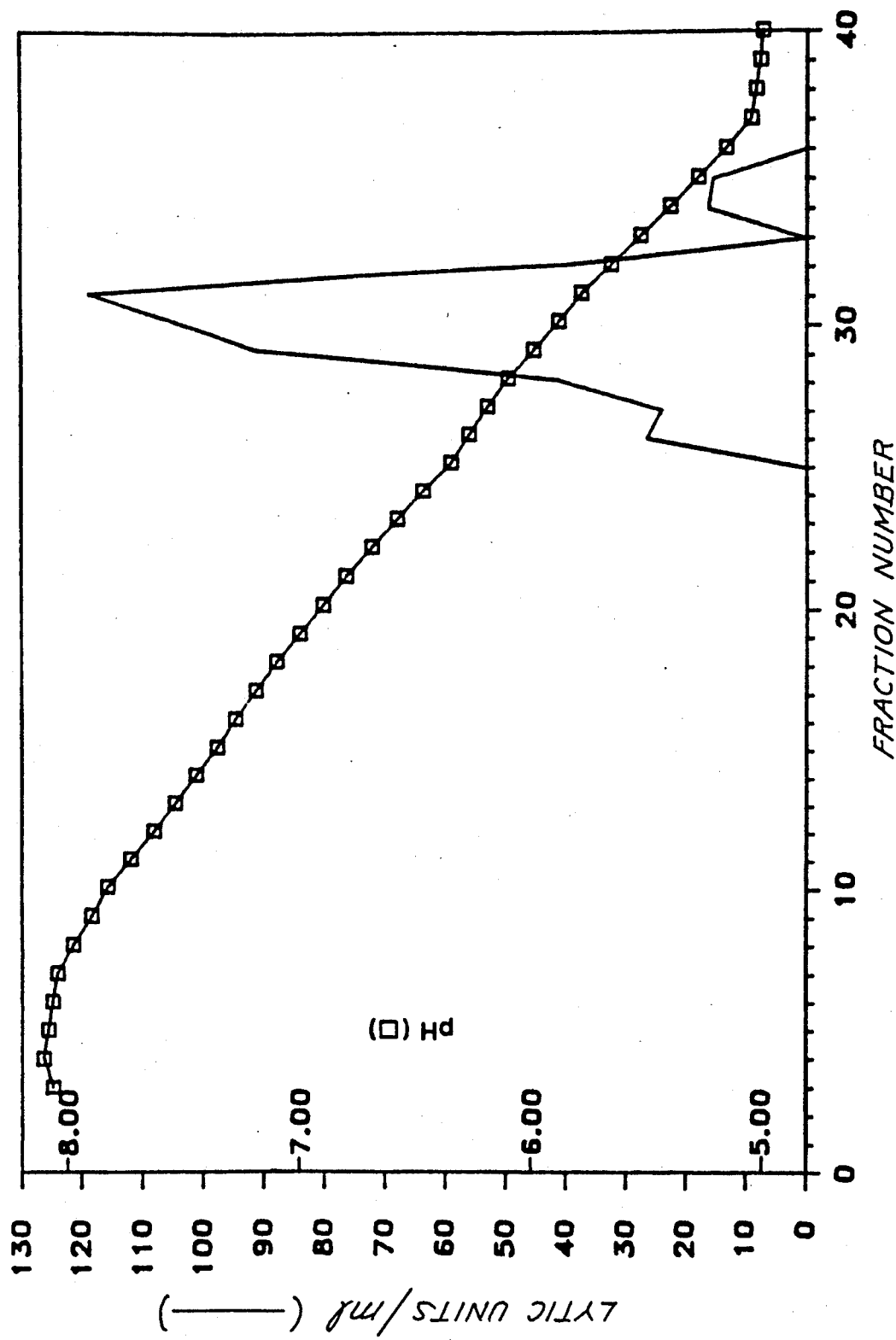
FIG. 11. A pool of beta-HMT obtained by molecular sieving of HMS on Sephacryl S-200 was subjected to chromatofocusing on PBE 94 using a pH 8–5 elution gradient. Each fraction was tested for biological activity on L-929 cells (−) and the pH determined (□).

Chromatofocusing of beta-HMT was carried out essentially according to the instructions of the manufacturer (Pharmacia). A 0.5×15 cm column of Polybuffer Exchanger 94 was employed. The start buffer was pH 8.3, 25 mM Tris-acetate into which the sieved beta-HMT in DPBS was diluted at a 1:10 ratio. Eluting buffer was pH 5 Polybuffer made with 30% Polybuffer 96 and 70% Polybuffer 74 diluted in deionized distilled water at a final concentration of 1:10. After the sample was loaded and initially washed with start buffer, the gradient using the eluting buffer was run. The pH of the eluted fractions was determined, and the cytotoxic activity of each fraction was determined by bioassay on L-929 cells. The predominant beta-HMT class obtained by molecular sieving was subjected to chromatofocusing on a Polybuffer Exchanger over a pH 8-5 gradient. As seen in FIG. 11, this lytic species eluted with a pH of approximately 5.8 thus indicating a pI of approximately 5.8 for beta-HMT.

B. Biochemical Characterization

1. Functional Characterization of B-HMT

The possible role of trypsin-like proteases, oxygen-dependent functions and arginase activity in B-HMT-mediated lysis of target cells was determined. B-HMT preparations were treated with various doses of TLCK and TAME, two known protease inhibitors. TLCK (alpha,N-tosyl-L-lysylchloromethylketone; Sigma, St. Louis, Mo.) was dissolved in 50 mM HEPES buffer adjusted to pH 7.4 and immediately reacted with samples of sieved B-HMT. A range of inhibitor concentrations from 5.0 to 0.2 mM was employed. After incubation for 1 h at 37°, the samples were dialyzed overnight and then assayed on L-929 cells, along with a non-inhibitor treated control preparation of B-HMT (beta-HMT). Similarly, alpha,N-tosyl-L-arginylmethylester (TAME;Sigma), catalase (Sigma) and arginine hydrochloride (Sigma) were diluted in 50 mM pH 7.5 HEPES buffer and coincubated with B-HMT on L-929 cells. The concentrations of TAME ranged from 5mM to 0.56 mM, the concentrations of catalase ranged from 2,000 U/ml to 222 U/ml, and for arginine hydrochloride they varied from 2000 ug/ml to 222 ug/ml. These doses of agents were not demonstrably toxic to the target cells. The extent of lysis in these coincubation experiments was compared to the lysis for B-HMT on target cells in the absence of added inhibitor.

Figure 12A:
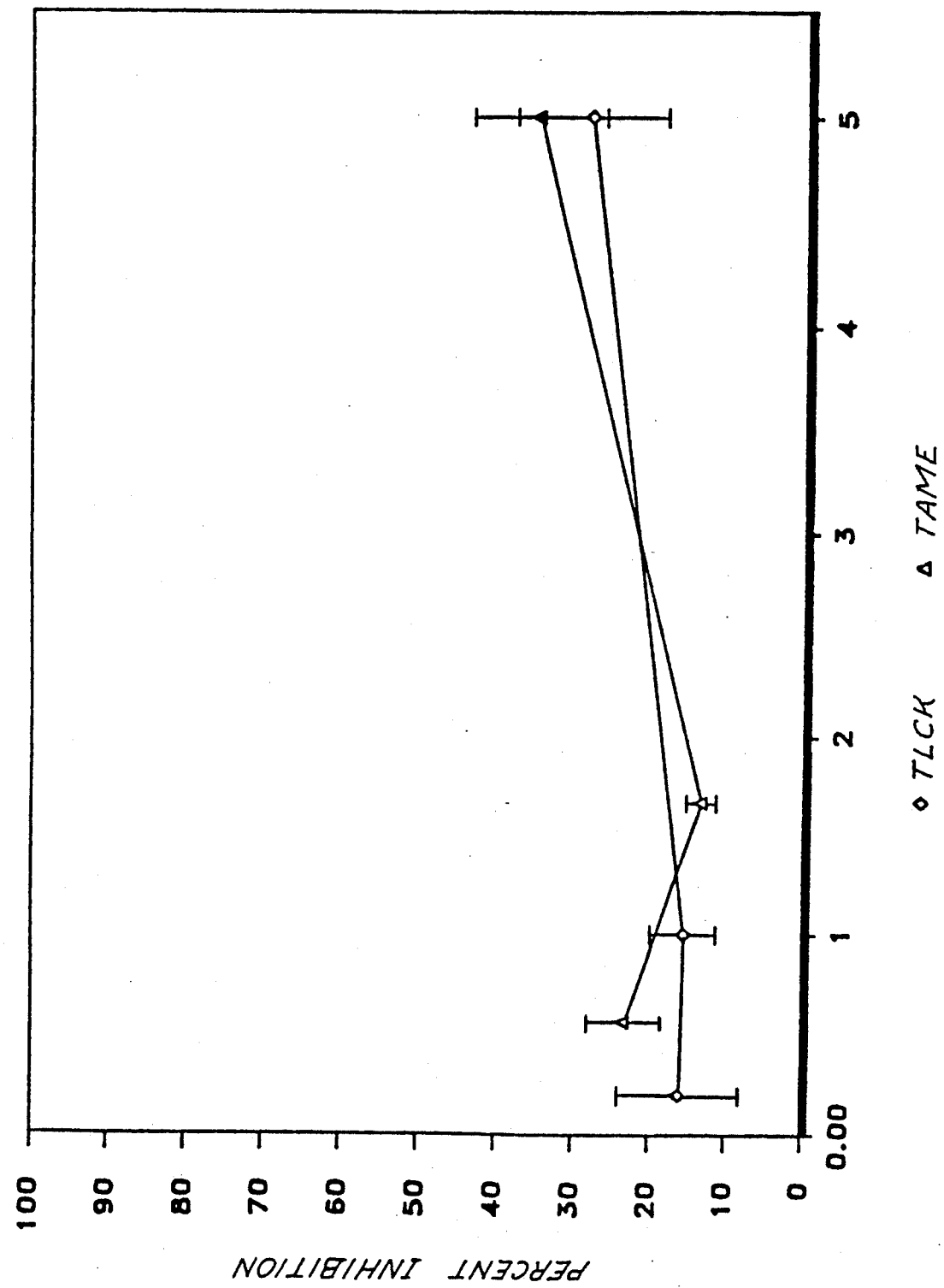
FIG. 12A. Beta-HMT was reacted with a dose range of TLCK (0.2–5.0 mM) for 1 hr. at 37° C.; after dialysis, the samples were assayed for lytic activity, and compared to a non-inhibitor treated control. Values shown for percent inhibition are mean ±SE (◇). Similar, TAME (0.67–5.0 mM) was coincubated with beta-HMT during lysis of target cells; lytic activity in the presence of inhibitor was compared to a non-inhibitor treated control. Values shown for percent inhibition are mean±SE (Δ).
Figure 12B:
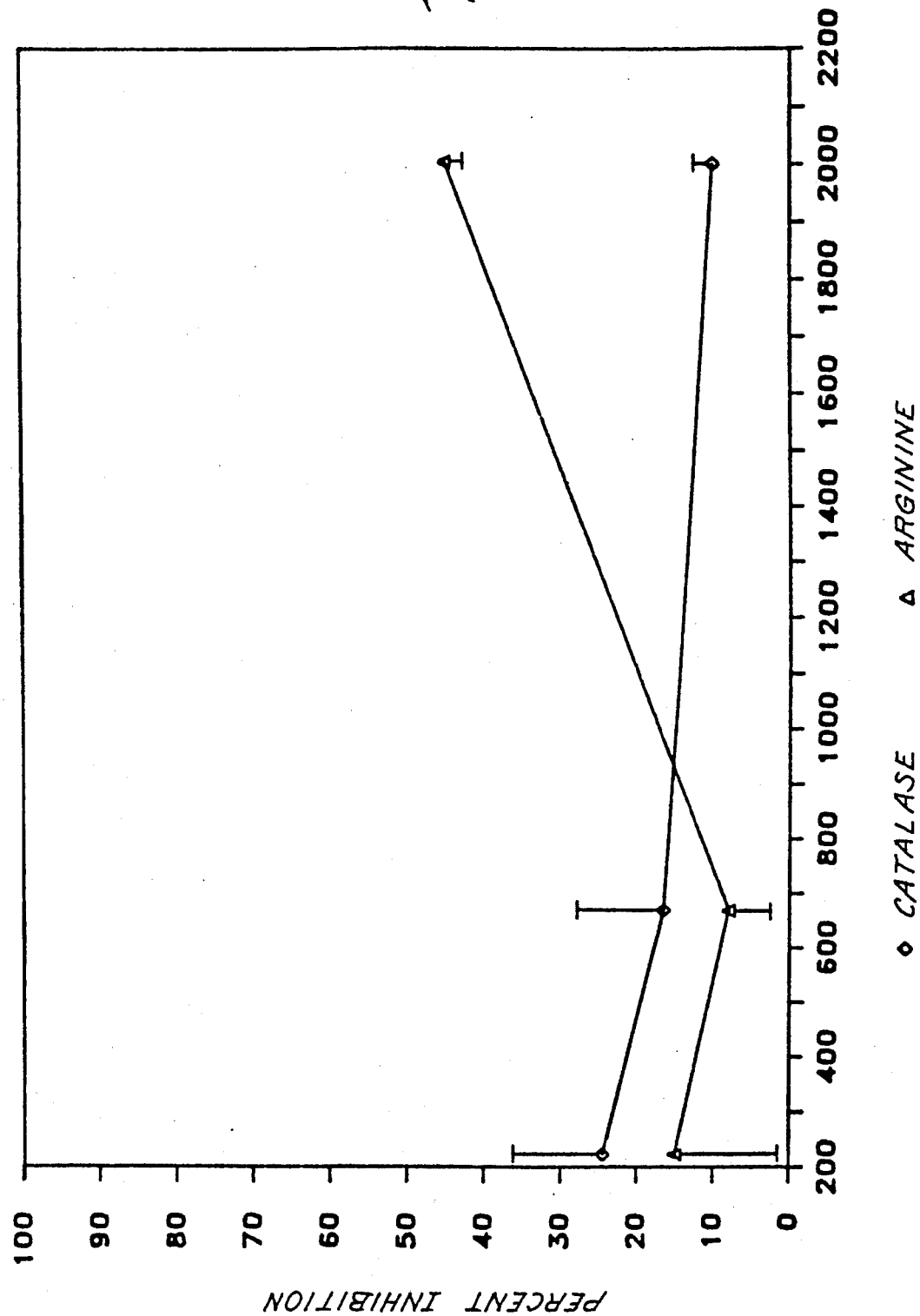
FIG. 12B. Beta-HMT was coincubated with a dose range of catalase (222–2000 units/ml) during lysis of target cells; lytic activity in the presence of enzyme was compared to a non-treated control beta-HMT preparation. Values shown for percent inhibition are mean±SE (◇). An identical approach was used for arginine (Δ).

The effect of these agents on the lytic activity of B-HMT is displayed in FIGS. 12A and 12B. Neither with the protease inhibitors TLCK or TAME, nor with catalase or high doses of added arginine, was a significant, dose-dependent inhibition of B-HMT lytic activity consistently observed.

Further evidence for the independence of B-HMT mediated cell lysis from mechanisms involving oxygen metabolites was obtained by measurement of $H_2O_2$ and $O_2^-$ produced during lysis. $H_2O_2$ and $O_2^-$ were measured by the microelisa method of Pick and Mizel ((1981), J. Immunol. Meth., 46:211. 2×10$^5$ L-929 cells in the presence of beta-HMT or beta-HMT alone was coincubated with either the $H_2O_2$ or $O_2^-$ reaction mixture. The $H_2O_2$ reaction mixture was 0.56 mM phenol red (Sigma) with 19 units/ml horse-radish peroxidase (Sigma) with or without 0.25 ng/ml PMA (Sigma) in Hanks balanced salt solution without phenol red. The $O_2^-$ reaction mixture was 1.2 mM ferrictochrome C (Sigma) with or without PMA in Hanks balanced salt solution without phenol red. Absorbance was determined on a microelisa reader (Dynatech, Alexandria, Va.) at 600nm for $H_2O_2$ (after alkalanization with 10 ul in NaOH) and at 550 nm for $O_2^-$. The reactions were monitored at 1.0, 4.0, and 18 hrs. of incubation at 37° C. Neither $H_2O_2$ nor $O_2^-$ were found to be produced in detectable amounts indicating that such pathways are not requisite for B-HMT activity.

2. Serological Characterization of Beta-HMT

The possible serological relationship of beta-HMT to recombinant human tumor necrosis factor (rHuTNF)

was determined employing a rabbit heteroantiserum against rHuTNF. This antiserum and rHuTNF were kindly supplied by Biogen. Two types of experiments were conducted. In the first, the amount of antiserum was held constant, while in the second type serial dilutions of the antiserum were used. Aliquots of rHuTNF or beta-HMT were added to microtiter wells. To these samples of toxins were added either media as a control or antiserum diluted to a final equivalent volume in media. These mixtures of toxins with a media control or with various levels of antiserum were allowed to incubate at room temperature for 1 hour. Thereafter, the lytic activity remaining in these preparations was determined by assay on L-929 cells. The lytic activity in those preparations which had received antiserum were compared to the lytic activity in those preparations which had received media only and expressed as a percentage thereof.

These results are shown in Table III. In the upper panel, when the antiserum level was held constant it neutralized the cell lytic activity of the rHuTNF (11,000 units/ml) to essentially undetectable levels in the biological assay. In contrast, it was not nearly as effective in neutralizing the cell lytic activity of beta-HMT (130 units/ml to approximately 40), a net reduction of 90 units/ml, which is about 100-fold less than with the rHuTNF. This difference in reactivity is further evident with titered antiserum, as seen in the lower panel. The lowest level of antiserum employed, the 1:125 dilution, effectively neutralized approximately 24,000 units of rHuTNF, and only about 75 units of beta-HMT; essentially complete neutralization is achieved with the higher levels of antiserum.

TABLE III

Anti-rHuTNF Antiserum Reactivity of Beta-HMT

| Antibody | | rHuTNF | Beta-HMT |
|---|---|---|---|
| Exp. 1 | (−) | 11,327 | 130[a] |
| | (+) | <15 (99.87%) | 39.4 (69.7%)[b] |
| Exp. 2 | (−) | 31,383 | 180 |
| | (+) 1:125 | 7,720 (75.4%) | 105 (41.7%) |
| | (+) 1:25 | <15 (99.95%) | <15 (91.7%) |
| | (+) 1:5 | <15 (99.95%) | <15 (91.7%) |

[a]Lytic Units/ml
[b]Percent Inhibition

3. Immunoprecipitation of beta-HMT and rHuTNF with and Anti-rHuTNF Antibody

Immunoglobulin isolated from the rabbit heteroantiserum against rHuTNF by protein A Sepharose affinity chromatography was used to immunoprecipitate beta-HMT and rHuTNF. Samples of beta-HMT or recombinant HuTNF (200–10,000 U/ml) were incubated with 10 ul of the anti-rHuTNF. After incubation at room temperature for 1 h., 100 ul of protein A Sepharose (Pharmacia) were added to each preparation. After further incubation for 1 h. at room temperature, the beads were subjected to centrifugation and multiple washing in DPBS. After washing, the beads were exposed to a buffer containing SDS and dithiothreitol, and these extracts, along with various molecular weight markers, were subjected to SDS-PAGE on a 5–15% slab gel system. After electrophoresis, the gels were subjected to silver staining.

The silver-stained slab gel revealed the expected 17 kD signal in the rHuTNF lane, along with the major heavy and light chain bands from the rabbit immunoglobulin. The immunoprecipitated beta-HMT sample demonstrated a significant unique peak at 60–70 kD, and no detectable band corresponding to rHuTNF in the 17 kD range. The remaining bands observed were apparently common between the rHuTNF and HMT lanes. In an additional lane, the rHuTNF was loaded directly onto the sample well without prior immunoprecipitation and served to further verified the extraneous nature of the additional bands which were common to the rHuTNF and HMT lanes.

By the foregoing disclosure, it is demonstrated that the HMTs released by LPS-triggered human peripheral blood monocytes (HPBM) are serologically related to rHuTNF but are apparently distinct from it. Two HMT species in the supernatant are detectable by molecular sieving, either on conventional or HPLC matrices. The higher molecular weight alpha form (100–120 kD) is typically present in very low amounts compared to the predominant beta form (60–70 kD). The beta form has been further characterized by a number of criteria.

Chromatofocusing of beta-HMT indicates that it has a slightly acidic pI, since it elutes from the Polybuffer Exchanger column at a pH of 5.8. Since beta-HMT is active in serum, and since neither TLCK nor TAME are capable of causing significant dose-dependent inhibition, it would appear that this molecule is not a trypsin-like protease. Cell lysis mediated by beta-HMT appears to be independent of oxygen-dependent mechanisms, since catalase is not capable of blocking lysis, nor is $H_2O_2$ nor $O_2^-$ produced in detectable amounts during the lytic reaction. The presence of arginine in the lytic assay medium and the only modest dose-dependent inhibition upon further addition of arginine, distinguishes beta-HMT from arginase.

The beta-HMT appears to be related to, but distinct from, human tumor necrosis factor (HuTNF) by a number of criteria. The first is the molecular weight as determined by molecular exclusion chromatography on Sephacryl S-200 or on HPLC sieving columns; beta-HMT migrates as a protein with a molecular weight of 60–70,000 Daltons. In contrast, the recombinant HuTNF (rHuTNF) migrates as a dimer of a 17,000 Dalton peptide, at 34,000, in physiological buffers. The second molecular distinction between beta-HMT and rHuTNF is isoelectric point. Beta-HMT is found to have a pI of 5.8 as determined by chromatofocusing, whereas recombinant HuTNF has a pI of about 5.3.

Additional evidence for the nonidentity for the two forms is obtained from serological characterization, using a rabbit antiserum raised against rHuTNF. Although beta-HMT is neutralized by this antiserum, much higher levels of this antiserum are required to achieve full neutralization, as compared to those levels required to block biological activity of the rHuTNF factor itself. One interpretation is that there are both common and distinct antigenic determinants between beta-HMT and rHuTNF. Another interpretation is that there are no identical determinants, but rather only slightly altered determinants for which this antiserum has lower affinity. Finally, using this antiserum against rHuTNF, immunoprecipitation of rHuTNF reveals a single peptide of 17,000 Daltons, in agreement with all other evidence. In contrast, a single peptide in the 60–70,000 Dalton range is precipitated by this antiserum with beta-HMT.

IV. Further Isolation Techniques

A. Antibody-Sepharose Chromatography

Alternatively, or in addition, to the foregoing fractionation and purification techniques, one may desire to purify the HMT factor by way of affinity purification, taking advantage of the immunoaffinity of anti-TNF antibody for beta-HMT. Such purification will provide an HMT population of very high purity.

In general terms, to accomplish the foregoing, the anti-TNF antibody is first bound to a matrix, for example, by conjugation to a Sepharose gel. Methods for binding antibodies to affinity matrices are well known in the art as, for example, detailed in *Methods in Enzymology*, Vol. 34B. One method for conjugation to Sepharose is as follows:

The gel is first washed with distilled water. A ratio of approximately 1 g of protein to 30 g of dry gel (dry weight equals approximately volume of wet packed gel divided by 1.6) is utilized. To one volume of wet gel add a volume of 2M $Na_2CO_3$, and stir slowly and chill to 5° C. Then add 2 g of cyanogen bromide per 30 g dried gel (CNBr; dissolved in $CH_3CN$ at 2 g/ml) to the chilled mixture and stir vigorously for 1-2 minutes. The mixture is then poured into a cooled sintered glass funnel and washed rapidly with 10-20 volumes of cold 0.1M $NaHCO_3$. One volume of 0.2M $NaHCO_3$ containing the dissolved protein is added and the mixture is stirred gently for 20 hours at 4° C. Then it is washed on a sintered glass funnel with 10-20 volumes of 0.1M acetic acid with 0.5M NaCl, then with 0.1M $NaHCO_3$ (pH above 8.0). Then, an equal volume of ethanolamine (1M in 0.2M $NaHCO_3$) is added and the mixture is stirred for about 4 hours. The mixture is then washed on a sintered glass funnel with 3M KCl in 0.1M sodium phosphate buffer, pH 7.0, and then with starting column buffer.

Next, an HMT-containing preparation is dissolved in a buffer in which it is stable with an appropriate ionic strength to allow for the formation of an antigen-antibody complex (e.g.—0.02M phosphate buffer, 0.25M NaCl, pH 7.6). It is then passed over the matrix-bound antibody using the same buffer. After washing the column to remove unbound material, the specifically bound HMT is eluted with one of several solutions, for example, 0.1M acetic acid followed by 0.5M acetic acid; 0.05M acetic acid, pH 2.5; 0.05M glycine-HCl buffer, pH 2.5; or 0.1M acetic acid followed by 6M urea. Where 6M urea is utilized, one will need to dialyze out the urea in a step wise fashion, for example, by reducing the urea concentration in the dialysate in molar increments.

B. Cloning of HMT Gene

It is further contemplated by the present inventors that the disclosure provided herein will allow the ability to obtain larger quantities of even further purified HMT material through the use of recombinant DNA technology. Recombinantly produced HMT can be obtained, in general, through the cloning and identification of the HMT gene using one of the various host/vector systems well known to those of skill in the art, taking advantage of biochemical attributes of HMT herein disclosed.

Such cloning can be accomplished by first preparing activated monocytes in the manner described above and using these activated monocytes as a source for mRNA that is thereby enriched for HMT mRNA. Thus, the enriched HMT mRNA fraction is obtained by first obtaining RNA from the activated monocytes and passing the RNA over an oligo-dT column to provide the poly-A containing RNA fraction (i.e.—mRNA). The HMT message-enriched mRNA fraction may then be further enriched by size fractionation of the mRNA, for example, by sucrose density centrifugation or column or reverse phase chromatography.

The enriched mRNA may then be "expanded" by injection into Xenopus oocytes by well known techniques. Those oocytes which are subsequently found to express HMT activity are collected and their mRNA fractions obtained in the same manner. This will provide larger amounts of enriched HMT mRNA for cloning directly by reverse transcription into cDNA or as molecular probes for screening existing recombinant DNA clone banks. Finally, clones which actively express the HMT factor may then be identified either by biological screening for the expression of HMT activity by the clones, or by screening with a labeled anti-TNF antibody.

V. Formulations and Dosages

For use in a clinical context, it will typically be desirable to formulate the purified HMT into an appropriate pharmaceutical vehicle. Such preparation will preferrably include extensive dialysis of the factor to remove ionic and other possible low molecular weight contaminants, followed by formulation with pharmaceutically acceptable salts in acceptable amounts. Salts should be included to maintain isotonicity of the preparation which will assist in maintaining the molecular integrity of the factor. Such solutions are typically buffered to maintain a neutral pH. Additionally, stabilizers in the form of, for example, sorbitol or stabilized gelatin may be included.

The HMT preparations should be administered in a manner compatible with the dosage formulation, and in such amount as will be therapeutically effective. The quantity to be administered depends on the subject to be treated in that the precise amounts of active ingredients required to be administered will depend on the judgment of the practitioner and will likely be peculiar to each patient. However, in that HMT exhibits an antitumor activity that is similar to TNF activity, reasonable doses, in terms of efficacy and patient tolerance, can be correlated with typical TNF doses presently used in animal tumor models, and in the clinic, for TNF administration.

Presently, TNF is undergoing clinical trials in order to determine a maximum tolerated dose (MTD) for TNF administration. In general, doses up to 7.5 to $10 \times 10^6$ units/m², for intramuscular or subcutaneous administration, or up to $2 \times 10^7$ units/m² for intravenous administration, have been tolerated. Moreover, the i.v. dose levels have not yet proven to be maximum, and higher doses will likely be tolerated as well. Accordingly, it is proposed that similar amounts of HMT, in terms of dosage units, will prove to be both useful and tolerated by cancer patients, wherein a unit is defined as the level of activity required to achieve a 50% killing in the L929 microassay as disclosed herein. This assay is the accepted microassay standard for the dosaging of TNF and similar antitumor activities, and may be employed for the dosaging of HMT formulations.

What is claimed is:

1. A method for providing a soluble antitumor factor that is distinct from tumor necrosis factor, comprising the steps of:
   (a) obtaining human cells of macrophage/monocyte lineage;
   (b) incubating the cells in an essentially endotoxin-free medium with an amount of a macrophage activating agent that is effective to trigger the release of the factor by the cells into the medium to a greater extent than release of tumor necrosis factor, to provide a factor-containing medium;

(c) separating molecules contained within the factor-containing medium according to their molecular weights or relative isoelectric points to provide a fraction which includes the antitumor factor essentially free of tumor necrosis factor and in a purified form relative to another fraction or fractions, the antitumor factor having an alpha form which exhibits a molecular weight of between about 100 and about 120 kilodaltons, or a beta form which exhibits a molecular weight of between about 60 and about 70 kilodaltons, upon molecular weight chromatography, the beta form being further characterized as follows:

(a) immunologically cross reactive with human tumor necrosis factor and having an isoelectric point of approximately 5.8; and (b) biologically active in the presence of catalase, arginine hydrochloride, TAME or TLCK.

2. A method for providing a soluble antitumor factor that is district from tumor necrosis factor, comprising the steps of:

(a) obtaining human cells of macrophage/monocyte lineage;

(b) incubating the cells in an essentially endotoxin-free medium with an amount of a macrophage activating agent that is effective to trigger the release of the factor by the cells into the medium to a greater extent than release of tumor necrosis factor, to provide a factor-containing medium;

(c) obtaining an antibody having specificity for human tumor necrosis factor, the antibody being affixed to a solid support, to provide a support-bound anti-tumor necrosis factor antibody;

(d) contacting the support-bound antibody with the factor-containing medium under conditions which will promote the formation of an immunocomplex between the antibody and the factor, to thereby provide a support-bound antibody/factor immunocomplex;

(e) washing the support-bound antibody/factor immunocomplex to remove non-specifically bound material; and (f) eluting the factor from the complex to provide the factor;

the antitumor factor having an alpha form which exhibits a molecular weight of between about 100 and about 120 kilodaltons, or a beta form which exhibits a molecular weight of between about 60 and about 70 kilodaltons, upon molecular weight chromatography, the beta form being further characterized as follows:

(a) immunologically cross reactive with human tumor necrosis factor and having an isoelectric point of approximately 5.8; and (b) biologically active in the presence of catalase, arginine hydrochloride, TAME or TLCK.

3. A method of activating cells of monocyte/macrophage lineage to release an antitumor factor that is distinct from yet immunologically cross reactive with human tumor necrosis factor and has a molecular weight of between about 60 and about 70 kilodaltons, the method comprising incubating the cells in an essentially endotoxin free medium with an amount of macrophage activating agent which is effective to trigger the release of the factor by the cells to a greater extent than the release of tumor necrosis factor.

4. The method of claim 1, wherein separating the molecules contained with the factor-containing medium according to their molecular weights or relative isoelectric points comprises subjecting the medium to molecular sieving or chromatofocusing, respectively.

5. The method of claim 2 or 3, wherein the macrophage activating agent is phorbol myristate acetate and the phorbol myristate acetate is present in the media in a concentration ranging from about 10 to about 1000 pg/ml.

6. The method of claim 2 or 3, wherein the macrophage activating agent is lipopolysaccharide and the lipopolysaccharide is present in the media in a concentration ranging from about 3 to about 5000 ng/ml.

7. The method of claim 2 or 3, wherein the macrophage activating agent is 6-O-stearoyl muramyl dipeptide and the 6-O-stearoyl muramyl dipeptide is present in the medium in a concentration ranging from about 30 ng/ml to about 10 ug/ml.

8. The method of claim 1, 2 or 3, wherein the essentially endotoxin-free medium comprises less than about 0.25 ng endotoxin/ml.

9. The method of claim 1, 2 or 3, wherein the macrophage activator agent comprises phorbol myristate acetate, lipopolysaccharide, or 6-O-stearoyl muramyl dipeptide.

10. The method of claim 1, 2 or 3, wherein the cells are primed with IFN-gamma prior to triggering.

* * * * *